(12) United States Patent
Robitzki et al.

(10) Patent No.: US 10,670,576 B2
(45) Date of Patent: Jun. 2, 2020

(54) DEVICE AND METHOD FOR MEASURING IMPEDANCE IN ORGANOTYPIC TISSUES

(71) Applicant: Universität Leipzig, Leipzig (DE)

(72) Inventors: Andrea Robitzki, Viernheim (DE);
Andrée Rothermel, Rimbach (DE);
Heinz-Georg Jahnke, Leipzig (DE);
Ina Sternberger, Magdeburg (DE);
Frank Striggow, Gerwisch (DE); Till Mack, Magdeburg (DE)

(73) Assignee: Universität Leipzig, Leipzig (DE)

( * ) Notice: Subject to any disclaimer, the term of this patent is extended or adjusted under 35 U.S.C. 154(b) by 368 days.

(21) Appl. No.: 15/408,649

(22) Filed: Jan. 18, 2017

(65) Prior Publication Data
US 2017/0191980 A1  Jul. 6, 2017

Related U.S. Application Data

(62) Division of application No. 12/392,045, filed on Feb. 24, 2009, now abandoned.

(30) Foreign Application Priority Data

Feb. 25, 2008  (EP) .................................... 08003365

(51) Int. Cl.
*G01N 33/483* (2006.01)
*G01N 27/04* (2006.01)
(Continued)

(52) U.S. Cl.
CPC ....... *G01N 33/4836* (2013.01); *G01N 27/041* (2013.01); *C12M 35/02* (2013.01); *C12N 13/00* (2013.01)

(58) Field of Classification Search
CPC ..... C12M 35/02; C12M 1/3407; C12N 13/00; G01N 33/4836
See application file for complete search history.

(56) References Cited

U.S. PATENT DOCUMENTS 5,178,096 A    1/1993  Lock et al.
5,624,537 A    4/1997  Turner et al.
(Continued)

FOREIGN PATENT DOCUMENTS

EP    1205541 A1    5/2002
EP    2103933 B1    7/2011
(Continued)

OTHER PUBLICATIONS

Andree Rothermel et al., *BioTechniques* (Oct. 2006), vol. 41: 445-450.

*Primary Examiner* — Jonathan M Hurst
(74) *Attorney, Agent, or Firm* — Chalin Smith; Smith Patent, LLC

(57) ABSTRACT

The present invention refers to a device for measuring impedance in organotypic tissue comprising at least one recording chamber with a liquid permeable membrane supporting the organotypic tissue, at least one bottom electrode and at least one top electrode, wherein the liquid permeable membrane divides the recording chamber into a top chamber and a bottom chamber, wherein at least the bottom chamber contains culture medium for the organotypic tissue, and the bottom electrode(s) is/are located in the bottom chamber and the top electrode(s) is/are located in the top chamber, and wherein the organotypic tissue is located between the bottom electrode(s) and the top electrode(s). The present invention also refers to the use of the device according to the present invention for measuring impedance in organotypic tissue. Furthermore, the present invention relates to a method for analyzing the effect of test compounds on pathological and non-pathological organotypic tissue by measuring the impedance of the organotypic tissue, wherein the organotypic tissue is cultured in a culture medium during the time of the analysis and the impedance of the organotypic tissue is measured at least once before and at least once (Continued)

after treating the organotypic tissue with the test compound or the impedance of the organotypic tissue treated with the test compound is compared to a non-treated organotypic tissue, wherein the impedance is measured using at least one electrode at each of two opposing sides of the organotypic tissue, and the electrodes are contacted with the culture medium or the tissue during measuring the impedance.

34 Claims, 11 Drawing Sheets

Specification includes a Sequence Listing.

(51) Int. Cl.
*C12M 1/42* (2006.01)
*C12N 13/00* (2006.01)

(56) References Cited

U.S. PATENT DOCUMENTS

| | | | |
|---|---|---|---|
| 6,387,671 B1 | 5/2002 | Rubinsky et al. | |
| 6,927,049 B2 | 8/2005 | Rubinsky et al. | |
| 6,936,462 B1* | 8/2005 | Owen | G01N 33/5438 435/287.7 |
| 2002/0092849 A1 | 7/2002 | Petrenko | |
| 2002/0137121 A1 | 9/2002 | Rubinsky et al. | |
| 2003/0033621 A1* | 2/2003 | De La Monte | A61K 49/0008 800/12 |
| 2004/0152067 A1 | 8/2004 | Wang et al. | |
| 2004/0208795 A1 | 10/2004 | Toi et al. | |
| 2005/0014130 A1* | 1/2005 | Liu | G01N 33/5008 435/4 |
| 2005/0170510 A1 | 8/2005 | Huang et al. | |
| 2006/0050596 A1* | 3/2006 | Abassi | C12Q 1/002 365/230.06 |
| 2007/0212773 A1 | 9/2007 | Fuji et al. | |
| 2008/0030206 A1 | 2/2008 | Podhajsky | |
| 2009/0053813 A1 | 2/2009 | Evans | |

FOREIGN PATENT DOCUMENTS

| | | |
|---|---|---|
| WO | WO 2004/010103 | 1/2004 |
| WO | WO 2005/077104 | 8/2005 |
| WO | WO 2006/047299 | 5/2006 |
| WO | WO 2006/104839 | 10/2006 |
| WO | WO 2007/015878 | 2/2007 |

* cited by examiner

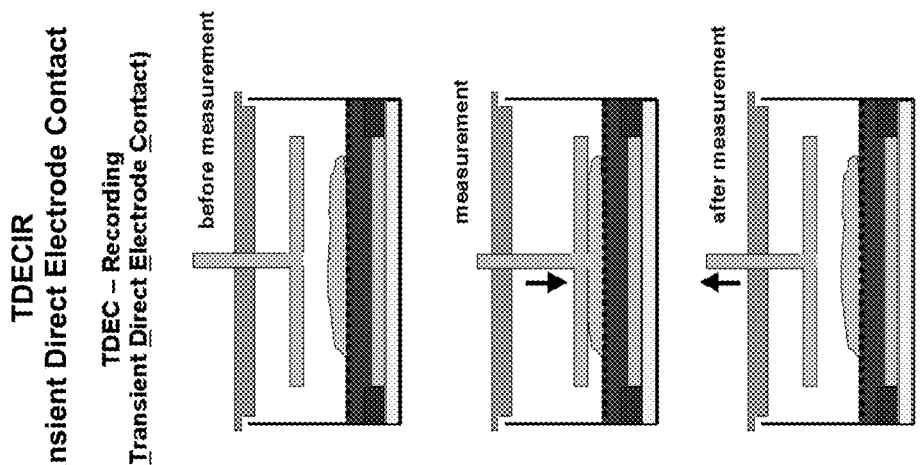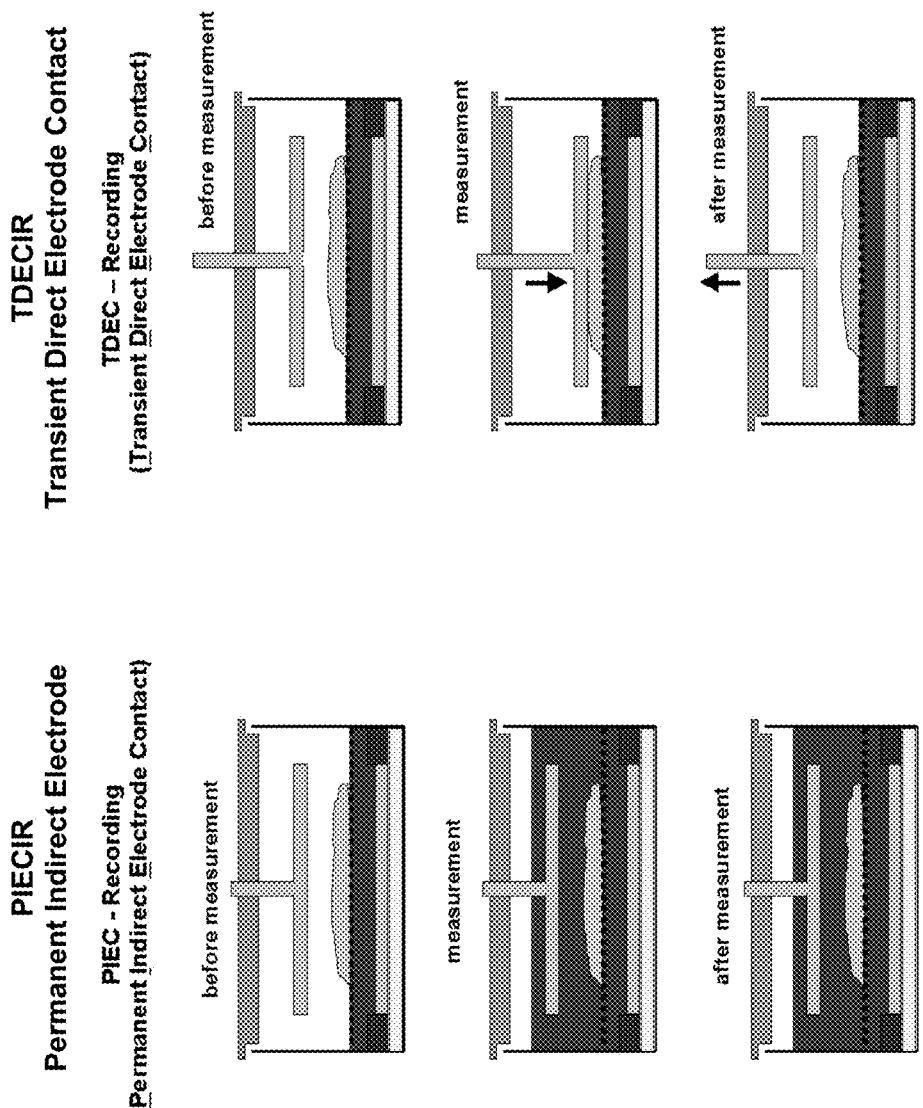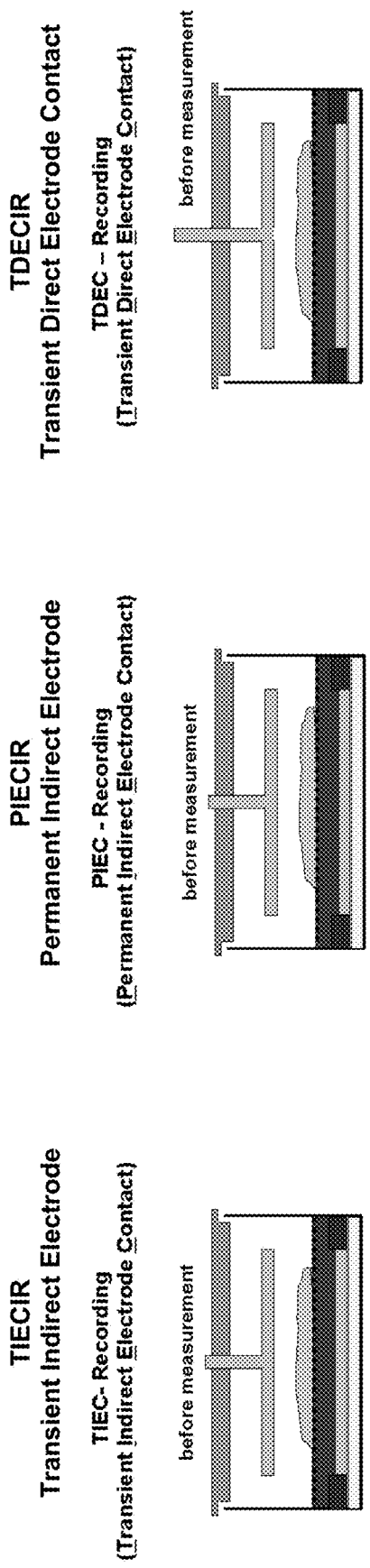

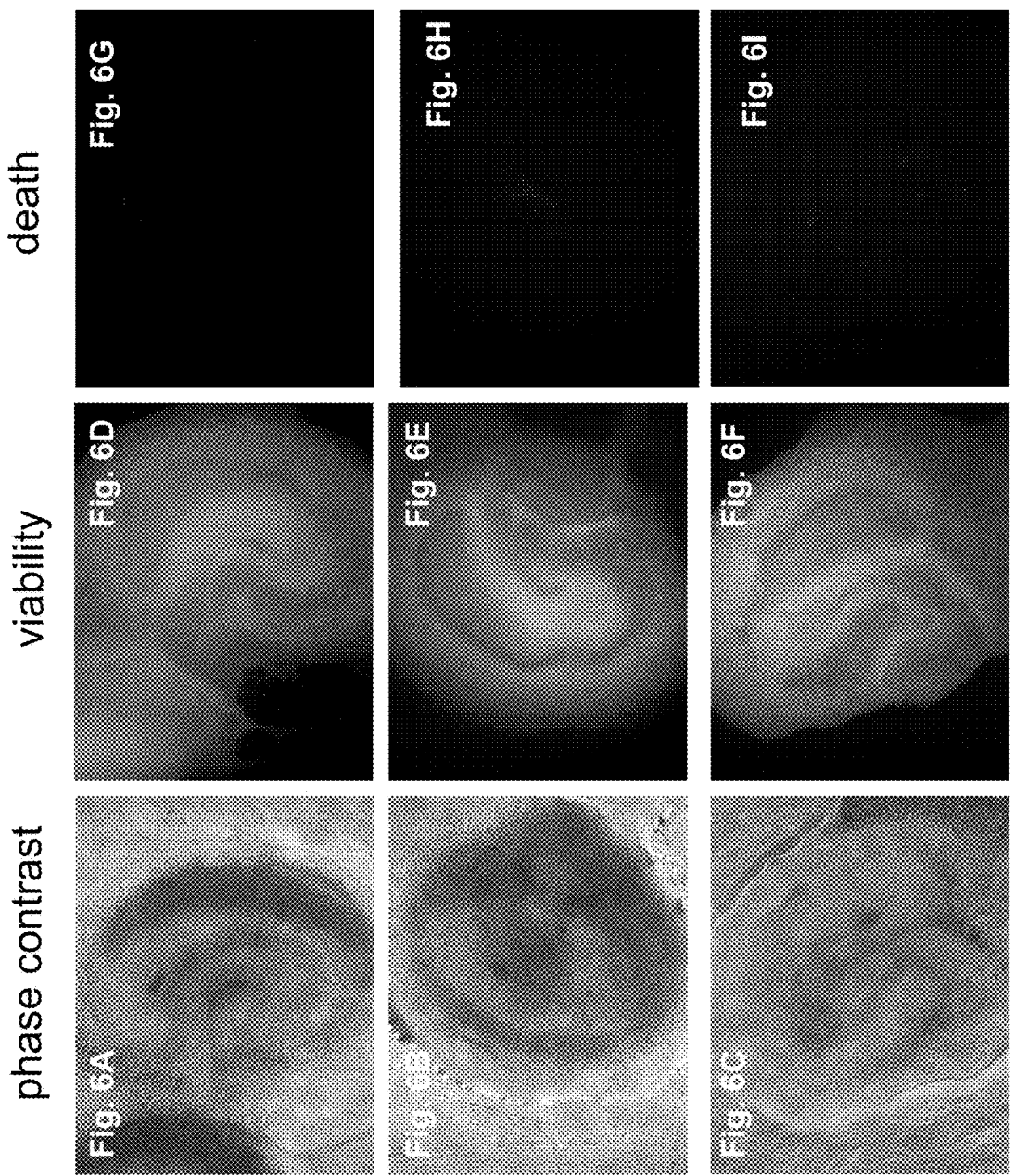

DEVICE AND METHOD FOR MEASURING IMPEDANCE IN ORGANOTYPIC TISSUES

PRIORITY

This application is a divisional of U.S. patent application Ser. No. 12/392,045, filed Feb. 24, 2009, which, in turn, claims priority to European Patent Application No. 08.003365.7 filed Feb. 25, 2008, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Feb. 2, 2009, is named LNK_045_SequenceListing.txt and is 7,710 bytes in size.

FIELD OF THE INVENTION

The present invention refers to a device for measuring impedance in organotypic tissue comprising at least one recording chamber with a liquid permeable membrane supporting the organotypic tissue, at least one bottom electrode and at least one top electrode, wherein the liquid permeable membrane divides the recording chamber into a top chamber and a bottom chamber, wherein at least the bottom chamber contains culture medium for the organotypic tissue, and the bottom electrode(s) is/are located in the bottom chamber and the top electrode(s) is/are located in the top chamber, and wherein the organotypic tissue is located between the bottom electrode(s) and the top electrode(s). The present invention also refers to the use of the device according to the present invention for measuring impedance in organotypic tissue.

Furthermore, the present invention relates to a method for analyzing the effect of test compounds on pathological and non-pathological organotypic tissue by measuring the impedance of the organotypic tissue, wherein the organotypic tissue is cultured in a culture medium during the time of the analysis and the impedance of the organotypic tissue is measured at least once before and at least once after treating the organotypic tissue with the test compound or the impedance of the organotypic tissue treated with the test compound is compared to a non-treated organotypic tissue, wherein the impedance is measured using at least one electrode at each of two opposing sides of the organotypic tissue, and the electrodes are contacted with the culture medium or the tissue during measuring the impedance.

BACKGROUND OF THE INVENTION

A prime example for neurological degenerations is represented by Alzheimer's disease (AD). AD is a devastating dementia affecting approximately 4 million people in Europe. It progressively destroys a person's memory, ability to learn, to reason, make judgments, communicate, and carry out daily activities. Up to date, there is no effective treatment or cure for Alzheimer's disease. On average, a person dies 8 years after the first symptoms arise. Patients are commonly treated with acetylcholinesterase inhibitors and/or NMDA-receptor antagonists. These drugs show modest clinical benefit in mild to moderate cases of Alzheimer. They are only efficient for up to 12 months, as their beneficial effects fade. Nevertheless, the market value for these drugs amounted to $ 4 billion in 2005 and is expected to rise to approximately $ 6 billions by 2010. More importantly, the National Institute on Aging estimated that medical care costs for the 4.5 million Alzheimer patients in USA amounted to $ 100 billion annually, rising to $160 billions by 2010. As the number of Alzheimer patients is expected to quadruplicate within the next 40 years, the increase in care costs may exceed the ability of health systems to absorb these costs. Therefore, the efficient and fast development of Alzheimer drugs is not only eagerly anticipated by patients and the pharmaceutical industry, but it is a necessity for all industrialized countries. The Alzheimer association estimated that a treatment that would efficiently delay the onset of AD for 5 years could save $ 50 billion annually in the US.

Given the complex pathological mechanisms, drug development programs for neurodegenerative diseases such as Alzheimer's disease (AD), Parkinson's disease, Multiple Sclerosis (MS), bovine spongiform encephalopathy (BSE), Creutzfeldt Jacob disease (CJD), and various retinal degenerations predominantly depend mainly on whole animal models which are very expensive, laborious, and time consuming. Analyses of drug effects or pathological mechanisms are predominately performed by cell-destructive procedures like immunocytochemical, molecular biological, and/or proteinchemical methods.

But also non-destructive and labeling free measuring principles like impedance spectroscopy are known. Changes in impedance can be caused by alterations of intracellular or extracellular processes that have been induced by e.g. transformation of non-pathological into pathological form. Although a large number of transgenic animal models, ex vivo cultures, or cell lines for neurodegenerative diseases have been established, up to now, impedance spectroscopy has not been used for the analysis of organotypic tissues e.g. tissues related to neuronal degenerations. In most instances impedance-based screening has been carried out on monolayer cultures, which have the disadvantage that they do not take into account the three-dimensional geometry of the in vivo situation.

Since impedance spectroscopy is a non-invasive method, long-term measurements can be realized without influencing cellular behaviour. Hence, the cellular read out reflects real time conditions without disturbing effects due to complex and long lasting physical procedures. The latter methods are well suited to study a broad range of biological and medical problems, however, in many cases the real cellular information dropped away since e.g. staining artifacts make it difficult or completely impossible to interpret the extracted cellular data. In principle, tracing of biological processes in living cells can be performed with modern labeling techniques, but hold the risk to falsify data due to the positioning of foreign substance within the cell itself.

Impedance spectroscopy—also known as cellular dielectric spectroscopy (CDS) or electric impedance spectroscopy (EIS)—can be used to measure frequency dependent alterations of passive electrical properties of single cells by applying defined alternate currents and/or voltages.

The bio-impedance of single cells can be measured with a working electrode and a counter electrode. Different cellular parameters such as the capacitance and resistance of the cell membranes as well as intracellular membranes of organelles, the resistance of the extracellular medium and intrinsic cytoplasm, the extracellular matrix and the contact between cell and electrode contribute to the overall cellular impedance. To analyze alterations of impedance of living cells, an alternate voltage is applied to a biological sample. Depending on the dielectric properties of sub-cellular compartments and molecules the applied current can flow from an active working electrode through the cells whereby the remaining current is collected by a counter electrode. Depending on the frequency of the applied voltage, alterations of certain cellular compartments can be identified.

In this context it is possible to discriminate cellular behaviour according to their dispersions which can be divided in α-, and γ-dispersion. The α-dispersion ranges from 1 Hz to 1 kHz and results from counter ions, glycocalyx, and from ion channels, whereas the β-dispersion (1 kHz-100 MHz) is due to the cytoplasm membrane, intracellular membranes (organelles), cytosol and proteins. Additionally, the γ-dispersion (100 MHz-100 GHz) is defined by the dielectric properties of free and bound water, relaxation of charged subgroups, and partially by protein-protein interactions. In particular, the frequency dependent measurement of manifold cellular alterations of both electrical and non-electrical active cells under non-destructive real-time conditions point out the infinite possibilities of this technique.

A commonly used impedance recording method is the so-called electric cell-substrate impedance sensing (ECIS) introduced by Giaever and Keese (Giaever, I., and Keese, C. R. Monitoring fibroblast behavior in tissue culture with an applied electric field. Proc Natl Acad Sci USA. 1984; 81(12):3761-3764; U.S. Pat. No. 5,178,096). For ECIS, cells have to grow on a small gold electrode implemented on the bottom of a culture dish. If an alternate voltage is applied between a small working electrode, attached cells, and a large counter electrode, an increased impedance can be observed at a given time and single frequencies. ECIS has been further optimized for automated, non-invasive, real-time, and high throughput analysis (WO 2007/015878; WO 2006/104839; WO 2005/077104; WO2004/010103; Wegener et al. Impedance analysis of epithelial and endothelial cell monolayers cultured on gold surfaces. J Biochem Biophys Methods. 1996; 32(3):151-170; Ciambrone et al. S. Cellular dielectric spectroscopy: a powerful new approach to label-free cellular analysis. J Biomol Screen. 2004; 9(6): 467-480). These impedance-based multi-well devices have been used for recording of healthy, non-pathological adherent cells (monolayer cultures) for detecting cell attachment, detachment, migration, cell-substrate interaction, blood-brain-barrier function, chemotaxis, toxicology, proliferation, ligand-receptor-interaction, and apoptosis after application of test substances. In each of these cases cells were cultured as monolayer and analyzed by impedance spectroscopy. However, measuring the impedance in monolayer cultures does not provide data referring to the three-dimensional structure of living tissue.

There are also several approaches using impedance-based sensors for use in living systems. Heroux and Bourdages have published an article entitled "Monitoring living tissues by electrical impedance spectroscopy" (Ann Biomed Eng. 1994 May-June; 22(3):328-37). The article refers to the development of an electrical impedance spectroscopy (EIS) probe for monitoring cellular changes in living animals. This probe comprises two slender (0.17 mm) electrodes connected to two miniature coaxial cables and fixed at a distance of 5 mm from each other using an insulating plate. For impedimetric analysis the probe was directly implanted in living animals for monitoring different tissues (brain cortex, liver, kidney, spleen, and muscle). Impedance recording was performed after pentobarbital-induced respiratory and cardiac arrest. However, the above described assays using living animals are not suitable for long term impedance measurements and do not provide an automated screening method for drug candidates for the treatment of specific diseases.

WO 2006/047299 discloses an organotypic slice assay that can be used to study neurodegenerative diseases. The invention includes the generation of brain slice cultures and their possible analysis by HPLC, ELISA, MALDI, SELEX, gene arrays, or immunochemical assays. The invention also describes electrophysiological recordings of action potentials by means of whole-cell voltage- and current clamp technique. However, WO 2006/047299 does not disclose a method or device for measuring impedance in organotypic tissue.

Since impedance-based recordings of organotypic cultures have not been possible so far, a device and method for simple, fast, cost effective, non-destructive, and free-free measurement of cellular parameters of pathological and non-pathological tissues especially obtained from different parts of the central nervous system of individual (animal or human being) is desired.

The methods and devices for measuring impedance in organotypic tissue as defined in the claims overcome at least some of the problems of the prior art.

SUMMARY OF THE INVENTION

The present invention relates to a device 38 for measuring impedance in organotypic tissue 35 comprising at least one recording chamber 29 with a liquid permeable membrane 28 supporting the organotypic tissue 35, at least one bottom electrode 26 and at least one top electrode 34, wherein the liquid permeable membrane 28 separates the recording chamber 29 into a top chamber 30 and a bottom chamber 31, wherein the bottom electrode(s) 26 is/are located in the bottom chamber 31 and the top electrode(s) 34 is/are located in the top chamber 30, and wherein the organotypic tissue 35 is located between the bottom electrode(s) 26 and the top electrode(s) 34. Preferably, the device 38 comprises at least 2, further preferred at least 10, further preferred at least 50, even further preferred at least 100 and most preferred at least 200 recording chambers 29. Preferably, the bottom chamber 31 is adapted to contain or receive liquid culture medium. Preferably, the liquid permeable membrane 28 comprises an opening 33 for handling liquid so that the culture medium 32 (for culturing the organotypic tissue 35) can be filled into the bottom chamber 31.

In a preferred embodiment of the device 38, the top electrode(s) 34 in the top chamber 30 is/are movable in at least two directions so it/they can be contacted with or removed from the organotypic tissue 35 or the culture medium 32.

In an especially preferred embodiment of the device 38, the electrodes 26 and 34 are interconnected by at least one multiplexer 3 and an impedance/gain-phase analyzer system 2.

In another preferred embodiment of the device 38, the liquid permeable membrane 28 extends through all the recording chambers 29.

In an especially preferred embodiment of the device 38, the bottom electrode(s) 26 are supported on a substrate 25 at the bottom of the recording chamber 29.

In another preferred embodiment of the device 38, the electrodes 26 and 34 are individually addressable.

In another preferred embodiment of the device 38, the recording chambers 29 are connected to an automated liquid handling system.

In another preferred embodiment of the device 38, the liquid handling system can provide a humidified atmosphere in the recording chamber 29 or the liquid handling system is placed in an $CO_2$ incubator.

In an especially preferred embodiment of invention, the device 38 comprises a bottomless multiwell frame 9 with 1-1000 wells, wherein each well defines one recording chamber 29.

In another preferred embodiment, the device 38 comprises a lid 36 which contains an implemented multiplexer board 8.

In another especially preferred embodiment of the device 38, the bottom electrodes 26 are connected to connection pads 22 via conductors, wherein the conductors are isolated from each other by a passivation layer comprising silicon nitrite, silicon oxide, polyimide, or viscose polymers.

In another preferred embodiment of the device 38, the number of bottom electrodes 26 in the recording chamber is 1 to 256, further preferred 2 to 256, further preferred 4 to 256, further preferred 20 to 256 and most preferred 56 to 256.

The present invention also relates to the use of the above defined device 38 for measuring impedance in organotypic tissue 35.

In an preferred embodiment of the invention, the impedance of the organotypic tissue 35 is detected before, during and after transformation of non-pathological organotypic tissue 35 into pathological tissue 35.

The present invention also relates to a method for analyzing pathological mechanisms by measuring the impedance in organotypic tissue during the transformation of non-pathological organotypic tissue into pathological tissue, wherein the transformation of the non-pathological organotypic tissue into pathological tissue is preferably carried out by introducing mutant genes by means of bacterial or viral vectors, knock out of genes related to specific diseases, or treatment with chemical agents. The genes encoding proteins are preferably relevant for a neurodegenerative disease, preferably AD. The organotypic tissues can be obtained from prenatal (embryonic), postnatal and adult animals.

In another especially preferred embodiment of the invention, the organotypic tissue represents a slice culture or explant culture derived from any mammal, vertebrate and invertebrate species of embryonic, neonatal, postnatal, and adult individuals. Further preferred, organotypic neuronal slice cultures (derived from any part of the brain or retina) are used as organotypic tissues.

In another preferred embodiment, the pathological organotypic cultures are obtained from prenatal (embryonic), postnatal and adult animals by transforming the non-pathological cultures in pathological cultures by knock out of genes related to any neurodegenerative disease, preferably AD, by RNA interference techniques.

The present invention further relates to a method for analyzing the effect of test compounds on organotypic tissue by measuring the impedance of the organotypic tissue, comprising (i) culturing the organotypic tissue in a culture medium during the time of the analysis; (ii) contacting the organotypic tissue with the test compound; (iii) optionally measuring the impedance of the organotypic tissue prior to step (iii); (iv) measuring the impedance of the organotypic tissue at least once after step (iii), wherein the impedance is measured using at least one electrode at each of two opposing sides of the organotypic tissue, and the electrodes are contacted with the culture medium or the tissue during measuring the impedance.

In a preferred embodiment of the method, the time span between the first impedance measurement before treating the organotypic tissue with the test compound and the last measurement of the organotypic tissue treated with the test compound is at least 1 week, further preferred at least 2 weeks and even further preferred at least 4 weeks.

In another preferred embodiment of the method, the impedance measurements of the organotypic tissue are continuously performed.

In an especially preferred embodiment of the method, the organotypic tissue represents a slice culture or explant culture derived from any mammal, vertebrate and invertebrate species of embryonic, neonatal, postnatal, and adult individuals.

In another preferred embodiment of the method, the pathological organotypic tissue is obtained by transformation of non-pathological organotypic tissue into pathological tissue. Preferably, the transformation of non-pathological organotypic tissue 35 into pathological tissue 35 is carried out by introducing mutant genes by means of bacterial or viral vectors, knock out of genes related to specific diseases, or treatment with chemical agents.

In one preferred embodiment of the method, the pathological organotypic tissues are generated by using stem cells carrying relevant mutations or mutations relevant for the onset and progression of any neurodegenerative disease, preferably AD.

In another preferred embodiment of the method, the impedance of the organotypic tissue 35 is measured before, during and after transformation of the non-pathological organotypic tissue 35 into pathological tissue 35 and before, during and after treating the organotypic tissue with the test compound.

In another preferred embodiment of the method, the organotypic tissue used for measuring impedance is non-pathological tissue and is treated with test compounds to test the toxicity of the test compounds.

In an especially preferred embodiment of the method, measuring impedance is performed by transient indirect electrode contact impedance recording (TIECIR), permanent indirect electrode contact impedance recording (PIECIR) or transient direct electrode contact impedance recording (TDECIR).

In another preferred embodiment of the method, the organotypic tissue is obtained from transgenic animals carrying mutation inducing properties of neurogenerative diseases selected from the group consisting of Alzheimer's disease, Parkinson's disease, Huntington's disease, amyotrophic lateral sclerosis, prion diseases, Pick's disease, fronto-temporal dementia, progressive nuclear palsy, corticobasal degeneration, multiple system atrophy, mild-cognitive impairment, ischemic stroke, multiple sclerosis, motor neuron diseases, nerve injury and repair, age related macular degenerations, rod-cone dystrophy, cone-rod dystrophy, retinitis pigmentosa, glaucoma, and other retina associated degenerations. Preferably, the pathological organotypic cultures are obtained directly from transgenic animals carrying relevant mutations or mutation relevant for onset and progression of any neurodegenerative disease, preferably Alzheimer's diseases, Parkinson's disease, Huntington's disease, amyotrophic lateral sclerosis, prion diseases, Pick's disease, fronto-temporal dementia, progressive nuclear palsy, corticobasal degeneration, multiple system atrophy, mild-cognitive impairment, ischemic stroke, multiple sclerosis, motor neuron diseases, nerve injury and repair, age related macular degenerations, rod-cone dystrophy, cone-rod dystrophy, retinitis pigmentosa, glaucoma, and other retina associated degenerations.

In another preferred embodiment of the method, the measuring of the impedance is carried out by recording of frequency dependent impedance magnitudes and phase angles before and after application of test compounds at multiple frequencies (1 Hz-100 MHz).

In another preferred embodiment of the method, the impedance is measured by using a device according to the present invention.

The device and method according to the present invention is suitable for measuring impedance in pathological or non-pathological organotypic tissue, wherein the three-dimensional structure of the tissue provides valuable information with respect to pathological mechanisms in the living beings or the effect of test compounds on living beings. The present invention provides a simple, fast, cost effective, non-destructive, and free-free measurement of cellular parameters of pathological and non-pathological tissues especially obtained from different parts of the brain. The use of tissue instead of only monolayers of cells allows to obtain data which reflect the three-dimensional structure of the tissue.

The device according to the present invention advantageously allows to use standard multiwell formats, which helps to decrease the costs for the manufacturing of the device. Furthermore, automated liquid handling systems and incubators can be used.

Furthermore, the device and method according to the present invention is suitable for screening drug candidates or toxic compounds. The device and method can furthermore be used to analyze the effect of drug candidates on pathological and non-pathological organotypic tissue. The treatment of non-pathological tissue with the drug candidates allows to determine unwanted side effects and thereby effectively improves the drug development and drug safety process.

The method and device according to the present invention allow the detection of cellular alterations by measuring impedance in organotypic tissue. The obtained impedance data are e.g. impedance magnitude and impedance phase which in turn can be used to calculate the real part of the complex impedance. Alterations of these parameters may provide information about the cellular status before and after application of a drug or a toxic compound or between pathological and non-pathological cultures.

BRIEF DESCRIPTION OF THE FIGURES

FIG. 2 shows the device 38, which is connected to a multiplexer 3, an impedance/gain-phase analyzer 2, and a computer 1. The device 38 comprises a $CO_2$-incubator 4, a multiwell frame 5 and biological samples (organotypic tissues 35).

FIGS. 5-A to 5-C describe different procedures for handling of organotypic tissues and impedance measurements.

FIG. 6-A to 6-I illustrate organotypic hippocampal slice cultures that have been obtained from 8-9 day old rats and subsequently cultured on a biocompatible membrane in a 6 well recording chamber. The figures show: organotypic slice cultures exposed to repeated medium overflow for 15 minutes (6-A, 6-D, 6-G) or 30 minutes (6-B, 6-E, 6-F); viability tested by diamino fluorescein diacetat (6-D, 6-E, 6-F); apoptosis tested by propidium iodide staining (6-G, 6-H, 6-I); control cultures which were not covered with medium (6-C, 6-F, 6-I); and cultures transiently covered with medium (6-A to 6-H).

DETAILED DESCRIPTION OF THE INVENTION

Figure 1:
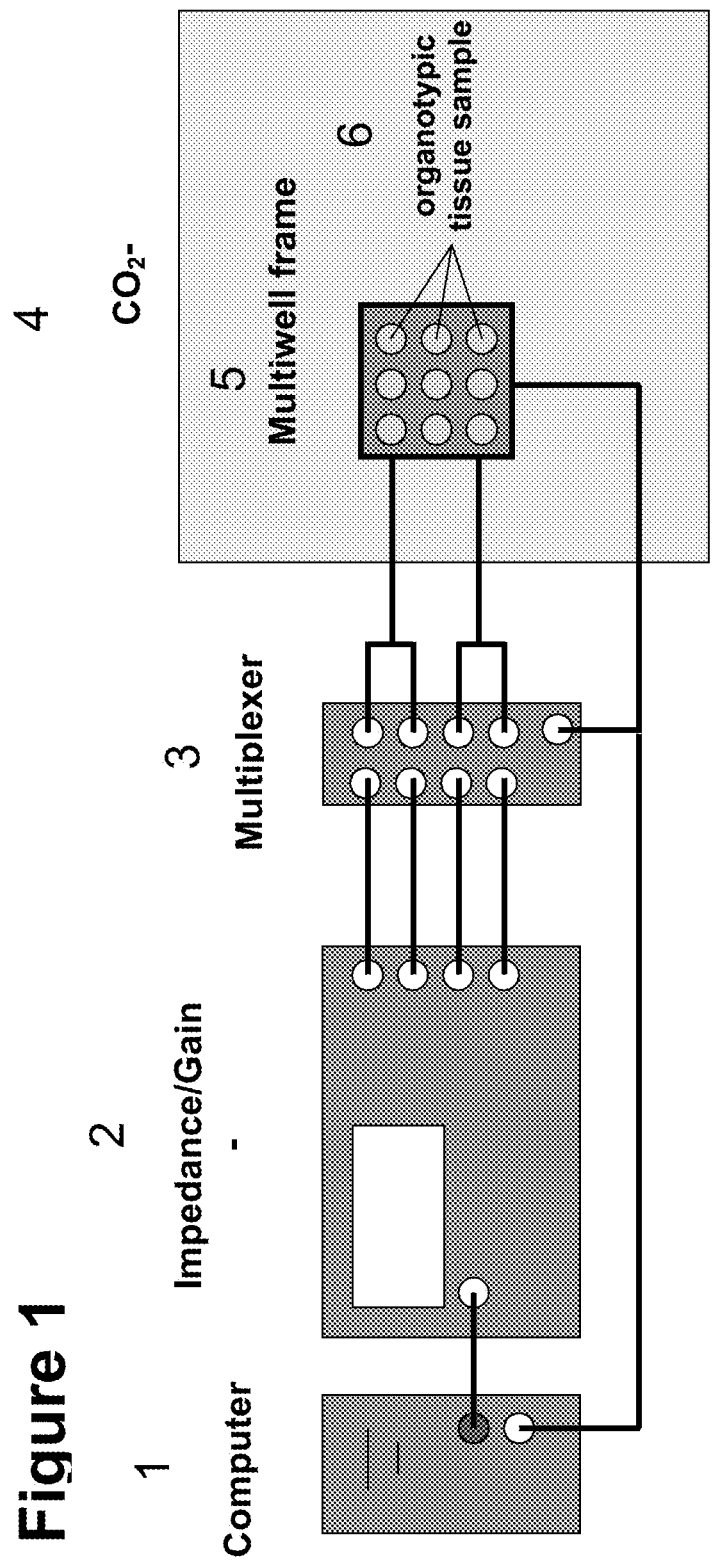
FIG. 1 is a schematic representation of a single recording chamber 29. The recording chamber 29 comprises a substrate 25, a bottom electrode 26, a passivation layer 27, a (biocompatible) liquid permeable membrane 28, a top chamber 30, a bottom chamber 31, a culture medium 32, an opening 33 in the liquid permeable membrane 28, a top electrode 34, an organotypic tissue 35, a lid 36, and a microchannel 37 in the lid 36.

Device for Measuring Impedance:

The device for measuring impedance in organotypic tissue comprises at least one recording chamber. Preferably, the device comprises at least 2, more preferably at least 6, more preferably at least 48 and most preferably at least 86 recording chambers. In the following, the expression "recording chambers" is used, wherein it is understood that devices with only one recording chamber are also included in the present invention. The recording chambers contain the organotypic tissue(s) which is/are subjected to the impedance measurement. The recording chambers furthermore contain a liquid permeable membrane, which spatially divides the recording chambers into a top chamber and a bottom chamber. The liquid permeable membrane mechanically supports the positioning and growth of the organotypic tissues. At least one bottom electrode is contained in the bottom chamber of the recording chamber and at least one top electrode is contained in the top chamber of the recording chamber. The organotypic tissue can be cultured in the recording chamber, which may contain a culture medium at least in the bottom chamber, and, depending on the method for measuring impedance (described in detail below) the culture medium can also be contained in the top chamber.

Bottom Electrodes:

During measuring impedance, the bottom electrode(s) is/are in direct contact with the culture medium or possess an additional layer which is in direct contact with the culture medium. The additional layer can be a polymer coating. Preferably, the bottom electrode(s) are in direct contact with the culture medium. In the following, we refer to the expression "bottom electrodes", wherein it is understood that also a recording chamber with only one bottom electrode can be used. The bottom electrodes are preferably connected to connection pads using conductors and the connection pads are preferably connected to a multiplexer.

The bottom electrodes can be made of any material having the necessary electric conductivity. Suitable materials for electrode based impedance measurements are known in the art. Preferably, the bottom electrode is made of gold, platinum, indium tin oxide ITO, silver, copper, iridium or alloys thereof. Depending on the used material, the thickness of the bottom electrodes is preferably between 10 nm and 1000 µm, further preferred between 50 nm and 100 µm, and most preferred between 100 nm and 10 µm.

The bottom electrodes are attached to the bottom of the recording chambers, wherein the recording chambers are preferably defined by a multiwell plate or multiwell frame. The bottom electrodes can be deposited on the bottom of the recording chambers by means of semiconductor technology. Electrodes can be sputtered onto silicon oxide, polyethylene (PE), glass, or comparable substrates. FIG. 8B shows the use of a multiwell frame which is placed on a substrate which forms the bottom of the multiwell frame. The multiwell frame can be glued, screwed, soldered, melted, clipped, or fitted to the substrate in order to provide a sealing which is liquid tight.

Preferably, universal microelectrode arrays are used. Those arrays consist of 384 single substrate-integrated microelectrodes arranged in a 24×16 format on the bottom plate of the device. Based on the arrangement of electrodes, the bottom plate represents an all-purpose device for all known multiwell formats. This means, the number of electrodes per well increases with the size of the well. For instance, a single well of a 6-well plate consists of 64 individual addressable electrodes, whereas a single well of a 384 well comprises only one electrode at the bottom. However, if necessary the electrode size can be adapted to the appropriate well size. In this case, a single well of an 6-well plate can consist of only one large electrode and not of 64 individual electrodes.

The bottom electrodes and conductors are electrically isolated from each other by a passivation layer 27. This passivation may consists of silicon nitrite, silicon oxide, polyimide, or viscose polymers such as SU-8 (Allresist GmbH, 15344 Strausberg, Germany). The thickness of the passivation depends on the used material and preferably ranges from 100 nm to a 20 millimeters. Preferably, the bottom area of the recording chamber covered by one ore more electrodes ranges from 20-100%. The electrodes can have any possible geometrical form such as round, squared, ring-like, etc.

Top Electrodes:

The top electrode(s) is/are located in the top chamber(s) of the recording chamber(s). In the following we refer to the expression "top electrodes", wherein it is understood that also recording chambers with only one top electrode can be used. The top electrodes can be made of the same materials as the bottom electrodes and preferably consist of gold or platinum. During measuring the impedance, the top electrodes are in direct contact with the organotypic tissue or the culture medium. The top electrodes can be of any shape suitable for measuring impedance. A skilled person is able to choose a suitable shape for the top electrodes. Preferably, the top electrode has a stamp-like shape or a pin-like shape, further preferred a stamp-like shape. Most preferably, every recording chamber contains only one top electrode.

In addition, the top electrodes can be movable in at least two directions so that they can be contacted with or removed from the organotypic tissue or the culture medium. Further preferred, the top electrodes are movable perpendicular to the liquid permeable membrane. In forward direction, the electrode can be positioned directly on the surface of the tissue or in the case of a small pin-like or needle-like electrode the top electrode can directly penetrate into the tissue. The close contact between tissue and top electrode is sufficient for the generation of an appropriate impedance circuit. After impedance measurement, the top electrode can be removed in the reversed direction to provide the upper surface of the tissue with oxygen, carbon dioxide and nitrogen. Positioning of the top electrode can be performed manually or automated by means of computer-assisted stepping motor. Destruction of tissue can be prevented by sensors detecting the pressure acting on the tissues. Alternatively, the exact position of the top electrode can be adjusted by measuring and analyzing the impedance or conductivity during moving the electrode towards the tissue. The changes of conductivity and impedance provide information about the intensity of the contact that has been generated between top electrode and tissue.

The top electrodes can be fixed to the device by any suitable means. Preferably, the top electrodes are integrated in a lid which covers the recording chamber(s).

Ground Electrodes:

The recording chamber(s) can additionally comprise ground electrodes in the bottom chamber. In this case, the bottom electrodes can be separated by ground electrodes to minimise parasitic interferences (increasing signal-to-noise ratio). The ground electrodes are connected via conductors to a ground pad. The ground electrodes are preferably stripe-shaped. Preferably, the ground electrodes are connected to a multiplexer.

Electrode Setup:

The electrodes (top, bottom, ground) are preferably individually or simultaneously, further preferred individually addressable. The top, bottom and additional ground electrodes are connected to the measuring devices via conductors. The electrodes and conductors are preferably made of gold, platinum, indium tin oxide, silver, copper, iridium or alloys thereof (which are suited for electrode based impedance measurements). The conductors can be isolated by silicon nitrite, polyimide or others materials. Preferably, the electrodes and conductors are additionally connected to a multiplexer and an impedance/gain-phase analyzer system. Preferably, the electrodes have a length of 1 mm to 20 mm. Preferably, the electrodes have a stamp-, pin-, needle-, or spike-like shape geometric structures. It is also preferred that the number of electrodes of an individual well is between 1 to 256, further preferred between 10 to 256, even further preferred between 30 to 256, and most preferred between 60 to 256.

The electrodes (top, bottom) can be electrically linked via connection pads to the impedance equipment (e.g. multiplexer, impedance/gain-phase analyzer). The ground electrodes are preferably linked via ground pads to the impedance equipment. For measuring impedance changes of organotypic tissues an alternate electrical current or voltage at single or multiple frequencies are applied at least to one pair of electrodes which includes a top and bottom electrode.

The height (thickness) of the electrodes is preferably between 50 nm and 1000 μm, and the diameter or width of electrodes is preferably between 10 μm and 10 mm. Also preferred is that the electrodes comprise interdigital electrodes. The electrode to electrode distance in the device is preferably at least 100 μm. The electrode area covering the bottom surface of an individual recording chamber is preferably between 5 and 90%.

The conductive elements (electrodes, conductors, connection/ground pads etc.) are preferably isolated from each other by a passivation layer preferably comprising silicon nitrite, silicon oxide, polyimide, viscose polymers such as SU-8, or any non-conducting materials suitable for passivation. Methods for isolation of conductive elements are well known in the art.

Liquid Permeable Membrane:

The liquid permeable membrane is biocompatible and mechanically supports the positioning and the growth of the organotypic tissue which is cultured in the recording chamber. The liquid permeable membrane can consist of any material that is compatible to cells or tissues without affecting cellular physiology. Preferably, the liquid permeable membrane consists of polyethylene, polycarbonate, aluminium oxide, nitrocellulose, mixed cellulose esters, hydrophilic PTFE (polytetrafluorethene), polyethylennaphtalate, teflon, regenerated cellulose, cellulose acetate, nylon, silicon, polyethersulfone.

The liquid permeable membrane is located in the recording chamber and divides the recording chamber into the top chamber and the bottom chamber. Preferably, the borders of the liquid permeable membrane are connected to the recording chamber in order to be mechanically stable. For gas and medium exchange, the liquid permeable membrane preferably contains pores. The pore sizes preferably range between 0.02 and 200 μm, further preferred between 0.02 and 100 μm, and most preferred between 0.02 and 10 μm.

Additionally, the membrane can possess at least one opening, which allows to e.g. exchange the culture medium in the bottom chamber and to add test compounds into the culture medium of the bottom chamber. Preferably, the opening has a diameter of 100 μm to 10 mm and is suitable for handling liquids. If the recording chamber comprises a lid, it is preferred that the lid also possesses such an opening (microchannel) in order to allow to add or remove liquids even if the lid is closed. Preferably, the handling of liquids is carried out by an automated liquid handling system. It is also preferred that the liquid permeable membrane is situated to each recording chamber by cell culture membrane inserts.

The pores allow the adequate diffusion and supply of the organotypic tissue with nutrients that are added into the culture medium which is at least in contact with the bottom side of the membrane. The membrane can be integrated between the top electrode(s) and the bottom electrode(s) at any horizontal position within the recording chamber.

In a preferred embodiment the liquid permeable membrane is suitable to induce pathological conditions in the organotypic tissue, which is in a non-pathological condition before culturing on the liquid permeable membrane. In order to induce pathological conditions, the liquid permeable membrane can be structured by photoactive lithography, soft lithography, laser ablation, printing, stamping, sputtering and chemical coupling of amino acids, peptides, proteins, enzymes, nucleic acids, carbohydrates, inorganic agents, organic agents, biological active molecules, pesticides, bacterias, fungis, yeasts, mycoplasms, body fluids etc and any combination of these test compounds which can be directly coupled or attached to the membrane. To improve the attachment of the ex vivo tissues the surface of the membrane can also be coated. Preferred coatings are fibronectin, collagen, laminin, polylysine, arginine, ornithine, but similar substances can be used for an improved adherence or to induce pathological effects.

Substrate:

The recording chambers can additionally comprise a substrate onto which the electrode(s), connection pads etc. of the bottom chamber can be deposited. The resulting substrate with the electrodes, conductors and connection pads deposited thereon can then be used as the bottom of the recording chambers or the multiwell array, respectively. The substrate can be made of glass, quartz glass, borsilicate glass, silicon, ceramic, polymer, polyimide, polypropylene, polystyrole, polyester, polycarbonate or any other material suited for sputtering electrodes and conductors. The thickness of the substrate depends on the material used for its preparation. If glass is used as substrate the thickness can vary from less than a millimetre to several millimetres. In case the substrate is a polymer, it can be used as a thin foil of a few 100 microns whereon electrodes can be deposited. The electrodes, conductors, and connection/ground pads are preferably integrated in the bottom substrate. Additionally, the substrate can comprise a thin foil on its surface to protect the electrical setup.

Lid:

The device according to the present invention can additionally further comprise a lid which covers each or all of the recording chambers, preferably, one lid can cover all the recording chambers. The top electrode or a plurality of top electrodes can be integrated in the lid, wherein the top electrodes are preferably movable as described above. Suitable lids can be fabricated by computer numerical control (CNC) based milling of biocompatible plastic or by plastic injection moulding and subsequent integration of electrodes by Microsystems Technology.

As described above, the lid preferably comprises an opening (microchannel) which allows to exchange culture medium or to add compounds to the culture medium in the bottom chamber, even if the lid is closed. The opening in the lid is preferably between 0.5 mm and 10 mm.

Impedance/Gain-Phase Analyzer:

The device according to the invention can comprise a commercial or custom impedance analyzer system. Such devices are well known in the art. HP4284, Hewlett Packard (USA); Solartron 1260A, Solartron Analyticals (UK); Agilent 4294A, Agilent Technologies Deutschland GmbH (Germany); IviumStat Analyser, IVIUM Technologies (The Netherlands).

Additionally, the impedance/gain-phase analyzer is connected to a computer to evaluate the obtained data.

Figure 2:
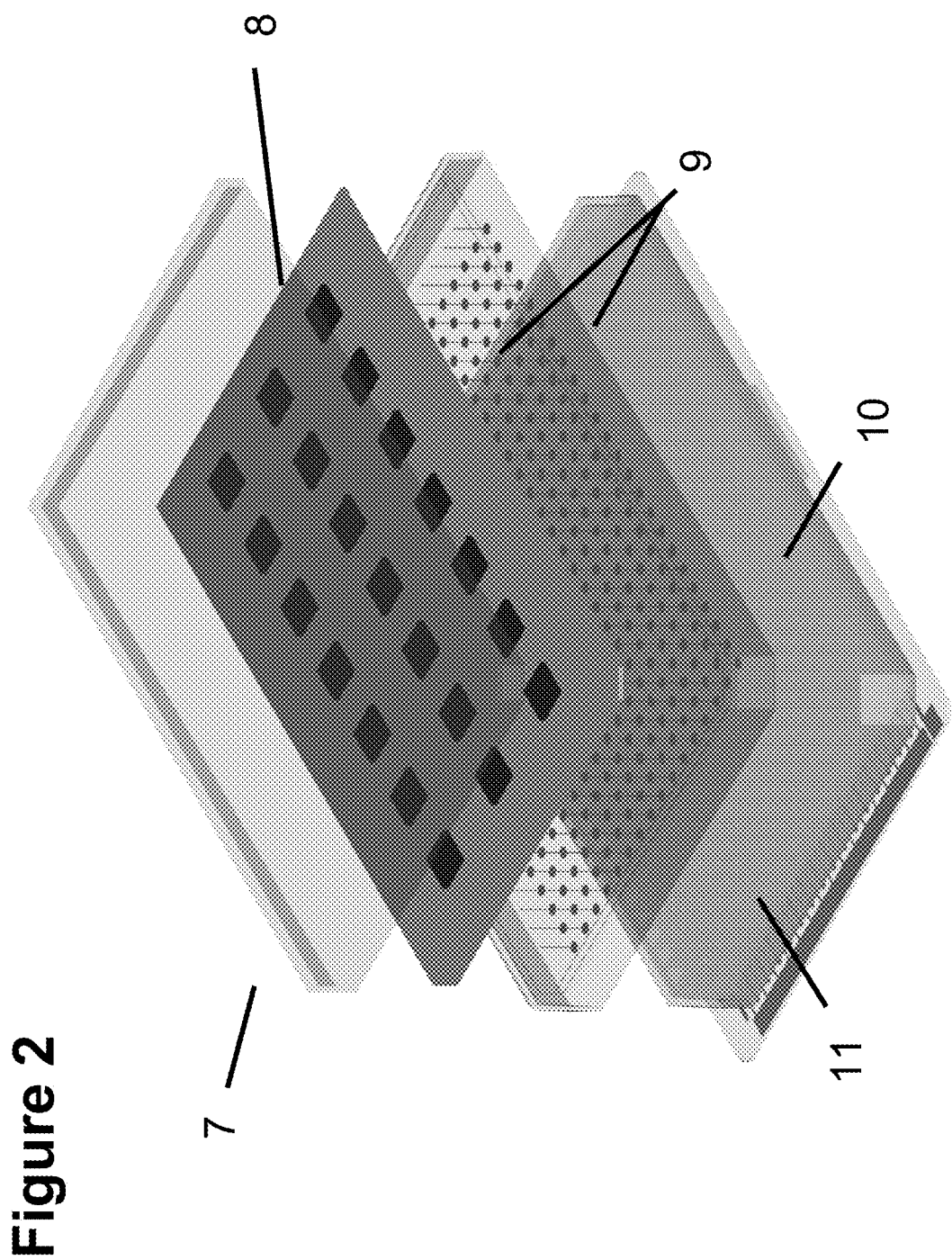
FIG. 2 describes a measuring setup that can be used to measure impedance of organotypic tissues 35.

Multiplexer:

Additionally, the device can be connected to a multiplexer, which itself is preferably connected to an impedance/gain-phase analyzer. The multiplexer is a device that performs multiplexing, which means that it selects one or more of many signals obtained from the electrodes of the device and outputs that signals in a suitable manner which have to be analyzed by the impedance/gain-phase analyzer (FIG. 2).

It is further preferred that the multiplexer is a multiplexer board and is integrated in the lid of the device. Suitable devices include, e.g., Multiplexer NI-SCXI-1153, National Instruments (USA); Electrode multiplexing Systems, ADG731, ADG725 from Analog Devices (USA).

Incubator and Liquid Handling System:

To realise a high reproducibility for high content or high throughput screening, especially for testing compounds (drug or toxic compounds) the device may combined with an automated liquid handling system that also provides a humidified atmosphere (e.g. 37° C., 5% $CO_2$, 95% air). Alternatively, the liquid handling system can be placed directly in a $CO_2$-incubator. Suitable Liquid Handling and Robotic systems are, e.g.: Freedom EVO®, TECAN Trading AG (Switzerland); Biomek FX Systems, Biomek® Assay Workstation, Beckman Coulter, (Germany); Biorobot 8000, Qiagen (Germany).

Multiwell Format:

Although the recording chambers and the device according to the present invention can be individually manufactured by skilled person to contain the above described means, the device preferably comprises commercially available multiwell plates or bottomless multiwell frames. It is even further preferred to use standard footprint multiwell plate formats according to the Society of biomolecular screening (SBS).

Figure 3:
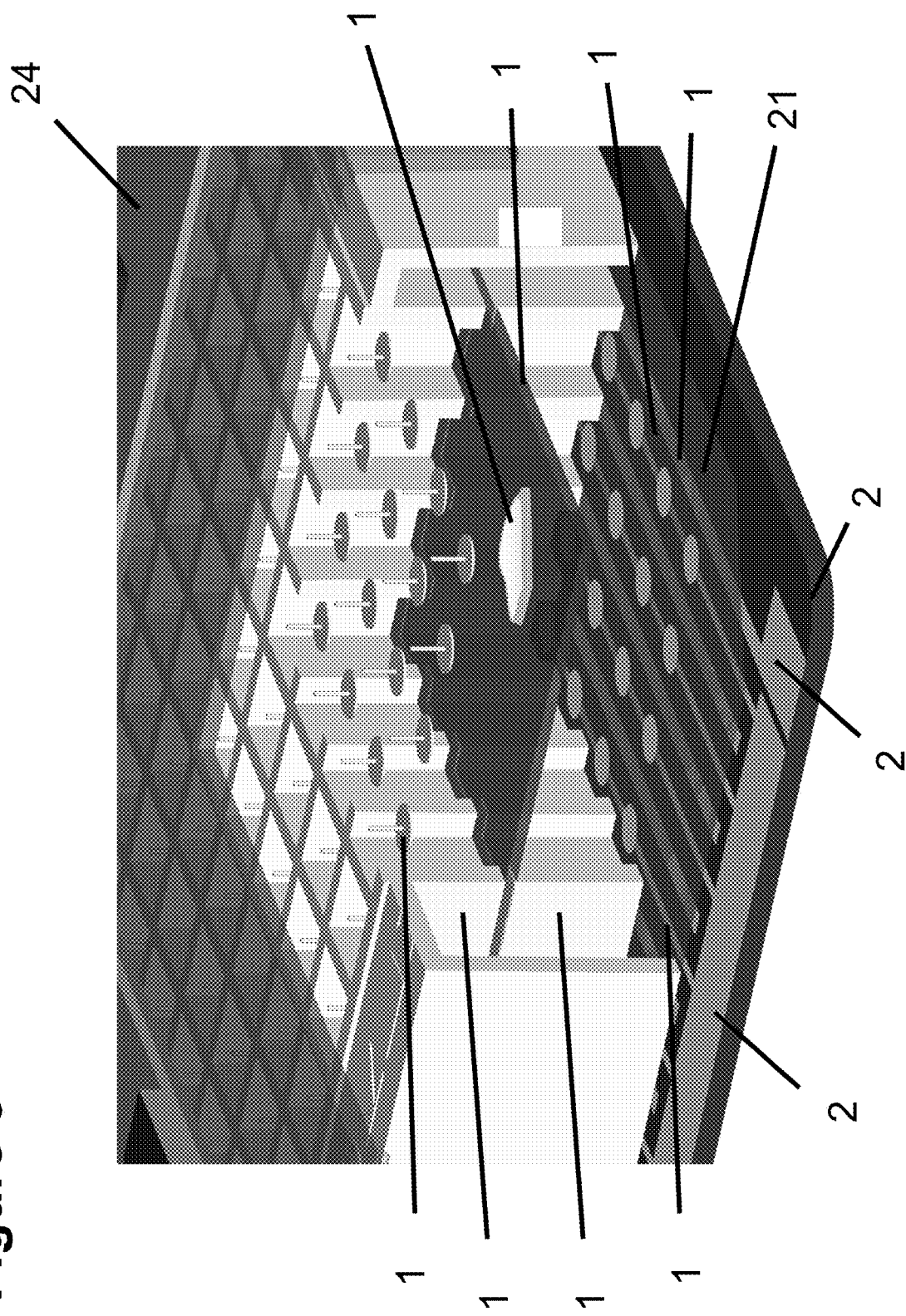
FIG. 3 depicts the assembly of a multiwell plate 9 for impedance recording of organotypic tissues 35. The electrodes and the liquid permeable membrane are not shown. The multiwell frame 5 comprises wells (not shown) and together with the glass substrate 25 defines the recording chambers 29 (not shown). On top of the multiwell frame 5 is a lid 36, which contains an implemented multiplexer board 8. The substrate 25 comprises connection pads 22.

Preferably, the device according to the present invention comprises a standard bottomless multiwell frame, wherein each well defines one recording chamber. According to this, a single 384 well plate comprises 384 recording chambers, a 192 plate consists of 192 recording chambers etc. Further preferred is the use of a bottomless multiwell frame with a plurality of wells, wherein the number of wells preferably ranges between 1 and 1000, further preferred between 6 and 384, further preferred between 86 and 384. Preferably, the device according to the present invention comprises a bottomless 6 to 384 standard multiwell frame. FIG. 3 discloses the use of a multiwell frame which is positioned on a substrate (preferably made of glass), which forms the bottom of the multiwell frame. The substrate and other means of the device are described in detail above. Preferably, the wells of the multiwell plates or multiwell frames have a diameter or width of 2 mm-35 mm and a height of 5 mm-30 mm.

The liquid-permeable membrane can be situated at any position in the bottomless multiwell frame. Preferably, the liquid permeable membrane covers all recording chambers of the complete bottomless multiwell frames at any position between the opposite ends of the bottom-less multiwell frame. For example, the liquid permeable membrane can be integrated horizontally in between to halves of the multiwell plate.

Depending on the used multiwell format, a different number of microelectrodes can be integrated in the top and bottom chamber. Each recording chamber contains at least one top electrode, at least one bottom electrode and can additionally contain at least one ground electrode. Accordingly, each recording chamber comprises at least two electrodes (top and bottom electrodes) e.g. per well of a 384 multiwell plate (384×2 electrodes, see FIG. 4). The recording chamber can also contain eight microelectrodes per well of a 96 multiwell plate (96×8 electrodes), or 16 microelectrodes per well of a 48 multiwell plate (48×8 electrodes), or 32 microelectrodes per well on a 24 multiwell plate (24×32 electrodes), or 64 microelectrodes per well of a 12 multiwell plate (12×64 electrodes), and 128 microelectrodes per well of a 6 multiwell plate (6×128 electrodes). Alternatively, the electrode sizes can be adapted to the appropriate well size. This means, one large top electrode and one large bottom electrode per well of the multiwell plate (6–384 well).

The electrodes of the multiwell plate can be interconnected by at least one multiplexer that controls either the top electrodes or the bottom electrodes, but it is also possible to multiplex both top and bottom electrodes at once. Furthermore, the ground electrodes are also connected (via conductors and ground pad) to the multiplexer and the computer (shown in FIG. 2).

The liquid permeable membrane can extend through all the recording chambers. Preferably, the liquid permeable membrane is placed on top of the multiwell frame which itself is placed on the substrate. The resulting chambers between the substrate and the liquid permeable membrane are the bottom chambers. The top chamber can be provided by using an additional multiwell frame which is placed on top of the liquid permeable membrane and defines the top chambers (see e.g. FIG. 4). The impedance measurement of organotypic tissues is described in detail below.

Organotypic Tissue:

The organotypic tissue which can be used for measuring impedance according to the method and/or device of the present invention can be non-pathological or pathological organotypic tissue. According to the invention, pathological organotypic tissue can either be directly derived from individuals suffering from the concerned disease (preferably neurodegenerative diseases) or can be derived from transgenic animals.

Neurodegenerative diseases or disorders according to the present invention comprise Alzheimer's disease, Parkinson's disease, Huntington's disease, amyotrophic lateral sclerosis, prion diseases, Pick's disease, fronto-temporal dementia, progressive nuclear palsy, corticobasal degeneration, cerebro-vascular dementia, multiple system atrophy, and mild-cognitive impairment. Further conditions involving neurodegenerative processes are, for instance, ischemic stroke, age-related macular degeneration, narcolepsy, motor neuron diseases, nerve injury and repair, and multiple sclerosis.

Preferably, the neurodegenerative disease is selected from the group consisting of Alzheimer's disease, Parkinson's disease, multiple sclerosis, amyotrophic lateral sclerosis, Huntington's disease, tauopathies and prion diseases. Most preferably, the neurodegenerative disease is Alzheimer's disease.

Additionally, non-pathological organotypic tissue can be used for the method or device according to the invention. Such organotypic tissue can then be transformed into a pathological form, preferably during the measurement or the effect of test compounds (e.g. toxic effects) on non-pathological organotypic tissue can be analyzed. The transformation of non-pathological into pathological organotypic tissue is described in detail below.

Organotypic cultures or explant cultures are preferably generated by using healthy (non-pathological) or pathological neurodegenerative model organisms of Alzheimer's disease, Parkinson's disease, Huntington's disease amyotrophic lateral sclerosis, prion diseases, Pick's disease, fronto-temporal dementia, progressive nuclear palsy, corticobasal degeneration, multiple system atrophy, mild-cognitive impairment, ischemic stroke, multiple sclerosis, motor neuron diseases, nerve injury and repair, age related macular degenerations, rod-cone dystrophy, cone-rod dystrophy, retinitis pigmentosa, glaucoma, and other retina associated degenerations, preferably AD.

In a preferred embodiment organotypic tissues can be generated and used for impedance measurements by stem cell-based tissue engineering.

The organotypic tissue preferably represents a slice culture or explant culture derived from any mammal (including primates and humans), vertebrate and invertebrate species of embryonic, neonatal, postnatal, and adult individuals. The mammal used as a tissue source can be a wild-type mammal or can be a mammal that has been altered genetically to contain and express an introduced gene. For example, the animal may be a transgenic animal, such as a transgenic mouse, that has been altered to express neural production of the β-amyloid precursor protein (Quon et al. (1991) Nature 35:598-607; Higgins et al. (1995) Proc Natl Acad Sci USA 92:4402-4406). In that embodiment, the animal will preferably be altered to express a β-amyloid precursor protein that is derived or based on human β-amyloid sequences. In one embodiment, the mammal used as a tissue source is a transgenic mammal that has been altered genetically to express tau protein or a variant thereof.

The mammal used as a tissue source can be of any age. In one embodiment, the mammalian tissue source will be a neonatal mammal. The mammal used as tissue source may have an age of about 1 to about 20 days, preferably of about 3 to about 15 days, more preferably of about 5 to about 12 days, still more preferably of about 7 to about 10 days, most preferably of about 8 to about 9 days.

A variety of donor tissues can be used for preparing slice or explant cultures. Dissection of organotypic neuronal slice cultures can be performed from any part of the brain or retina. Organotypic tissues of the retina can be cultured either as slice cultures or in toto, whereas brain tissues are usually generated as slices cultures. The terms "slice culture" or "organotypic tissue" or "ex vivo tissue" refers to sections of living tissue that can be cut in different orientations (anterior-posterior, dorsal-ventral, or nasal-temporal) and thickness. The term "explant" describes a living tissue or a piece of it that retains the original thickness and cellular morphology. For example, retinal explants can be obtained from different regions, which include the dorsal, ventral, nasal, or temporal part of the retina.

As used herein, the term "brain slice culture" means "organotypic brain slice culture" and refers to sections or explants of brain tissue which are maintained in culture. A skilled person can readily employ known methods for preparing organotypic brain slice cultures. Organotypic brain slice cultures can be derived from sections of the whole brain tissue or from explants obtained from specific regions of the brain. Any region can be used to generate an organotypic brain slice culture. However, the preferred source of the organotypic brain slice culture is explants obtained from specific regions of the brain, preferably the hippocampus region. Most preferably, the brain slice contains pyramidal neurons. Neuronal organotypic tissue can also be obtained from retina explants, wherein small retinal pieces can be used either from central or peripheral parts of the retina.

Any mammal can be used as a tissue source for the explant that is used to generate the organotypic tissue (preferably organotypic brain or retina slice culture) as long as the animal can serve as a tissue source and the organotypic slice culture can be established and maintained for a period sufficient to conduct the present methods. Such mammals include, but are not limited to rats, mice, guinea pigs, monkeys and rabbits. Usually, the mammal is a non-human mammal. The method of the invention may further comprise the step of obtaining an organotypic tissue from the mammal, or providing an organotypic tissue culture. The method may further comprise the step of culturing or cultivating the organotypic tissue prior to the impedance measurement.

The organotypic tissues can be cultured on biocompatible liquid permeable membranes, which are integrated horizontally in between to halves of the multiwell plate. In another embodiment, the organotypic culture can be pre-cultured on a common membrane insert of a culture dish, which may subsequently transferred to the recording chamber for impedance measurement.

Methods for the generation of slice or explant cultures have been reported in a number of previous studies (Förster et al., Hippocampal slice cultures, BioValley Monogr. Basel, Karger, 2005, 1:1-11, Eds. Poindron, Piguet, Förster; Hofmann et al., Organotypic cultures of the rat retina, BioValley Monogr. Basel, Karger, 2005, 1:58-73, Eds. Poindron, Piguet, Förster Li et al., 1993, Neuroscience 52(4):799-813; Stoppini et al., 1991, J Neurosci Methods 37:173-182; Gahwiler, 1988, Trends Neurosci 11:484-490; Seil (1979) Review in Neuroscience 4:105-177) and are well-suited for maintaining organotypic tissues on the said membrane of the said recording chamber (FIGS. 1 and 5A to 5C).

The preparation of organotypic tissue for use in the present invention is described in the following. The brain and retina are isolated as fast as possible and preferably transferred into physiological dissection media (e.g. MEM buffered with 10 mM Tris pH 7.2 for brain tissue and HEPES buffered F12 nutrient mix for retinal explants) supplemented with antibiotics. Suitable culture medium for impedance measurements are known in the art. The choice of culture medium and culture conditions depends on the intended use, the source of tissue, and the length of time before the section is used in the present method. Examples of culture media include, but is not limited to 25% horse serum, 50% minimum essential media, 25% Hank's media, supplemented with antibiotic and L-glutamine. Examples of culture condition include, but are not limited to, 37° C., 5% $CO_2$.

Cultures can be maintained for up to 8 weeks, under ideal conditions. However, organotypic brain slice cultures are preferably used after they have stabilized following the trauma of transfer to culture, but before onset of decline. In general, it is preferable to use the slice cultures from about 1 week to about 4 weeks after they have been generated.

Subsequently, brain and retina are cut into small pieces. Small regions are separated from the tissue as slices or explants such that the surface to volume ratio allows exchange between the center of the tissue and the media. A variety of procedures can be employed to section or divide the brain tissues. For example, sectioning devices can be employed. The size/thickness of the tissue section will be based primarily on the tissue source and the method used for sectioning/division. For example, preferred segments are from about 200 to about 600 µm, preferably from about 300 to about 500 µm, most preferably from about 350 µm to about 450 µm in diameter and are made using a tissue chopper, razor blade, or other appropriate sectioning/microtome blade. Retinal slices can be cut into slices of 100-400 µm thickness. Brain slices, small retinal pieces or slices are transferred to the said membranes. The recording chamber of the multiwell plate is filled with culture medium up to the bottom line of the tissue slices or explants.

Although different culture media can be used, the preferred media for brain slices consists of 50% minimum essential media, 25% Hank's media, and 25% horse serum whereas retinal explants can be maintained in DMEM containing 10% foetal calve serum. Both media are supplemented with L-glutamine and antibiotics. Depending on the type of tissue and experimental strategy other culture media can be used. If medium is exchanged every two days e.g. brain slices can be maintained for up to 8 and retinal explants for up to 6 weeks in a humidified atmosphere (95% air, 5% $CO_2$ and 37° C.). In each case, it is necessary to maintain the tissue within an air-liquid interface, which means that the organotypic tissues are not covered by medium but are supplied with culture medium from the bottom chamber. At least one slice or explant can be cultured on the membrane. In another embodiment multiple slices or explants can be cultured on a single membrane. In another preferred embodiment for impedance measurements co-culturing experiments can be performed by culturing slices or explants from different parts of the brain or from at least two different tissue sources (e.g. retina and brain or retina, brain and pigmented epithelium). In each of these cases the organotypic tissue or tissues pieces cover a membrane area ranging from 1%-100%.

Transformation of Non-Pathological into Pathological Organotypic Tissue:

Transformation of non-pathological into pathological organotypic tissue can be achieved by: (i) introducing mutant genes by means of bacterial or viral vectors, wherein these genes may encode proteins that are relevant for the development of the concerned diseases (relevant proteins for the development of AD are e.g. tau, APP, secretases); (ii) knock out of genes related to the concerned diseases (preferably AD) by RNA interference techniques; (iii) by any chemical agents that are capable to induce specific pathological mechanisms of the above described diseases (preferably AD). For example pathological mechanisms of AD can be induced by tau-hyperphosphorylation using ocadaic acid.

The methods (i) and (ii) require to introduce polynucleotides into the organotypic tissue and the cells thereof respectively. This is commonly achieved by transfection or transduction methods known in the art. The methods for transforming non-pathological organotypic tissue using the tau protein and APP are described in detail below.

Transfection and Transduction:

As used herein, the term "transduction" is used to describe the delivery and introduction of polynucleotide to eukaryotic cells using viral mediated delivery systems, such as, adenoviral, AAV, retroviral, or plasmid delivery gene transfer methods. These methods are known to those of skill in the art, with the exact compositions and execution being apparent in light of the present disclosure.

As used herein, the term "transfection" is used to describe the delivery and introduction of polynucleotide to a cell using non-viral mediated means, these methods include, e.g. calcium phosphate- or dextran sulfate-mediated transfection; electroporation; glass projectile targeting; and the like. These methods are known to those of skill in the art, with the exact compositions and execution being apparent in light of the present disclosure.

Preferably the transfection or transduction is transient. This generally refers to transient expression of the DNA construct introduced into the cells. The expression of the tau protein or the variant thereof usually peaks at around day 7-8 post transfection or transduction.

Transfection or transduction is preferably performed about 3 days to about 10 days, preferably about 4 days to about 6 days after the organotypic tissue culture has been prepared. It is further preferred that the impedance of the organotypic tissue is measured during the transfection or transduction.

A "vector" is a replicon, such as plasmid, phage, cosmid, or virus to which another polynucleotide segment may be operably inserted so as to bring about the replication or expression of the segment. The vector may particularly be a plasmid, a cosmid, a virus or a bacteriophage used conventionally in genetic engineering that comprise a polynucleotide encoding e.g. tau protein or a variant thereof. Expression vectors derived from viruses such as retroviruses, vaccinia virus, adeno-associated virus, herpes viruses, or bovine papilloma virus, may be used for delivery of the polynucleotide or vector into the cells of the organotypic tissue. Methods which are well known to those skilled in the art can be used to construct recombinant viral vectors; see, for example, the techniques described in Sambrook et al., "Molecular Cloning, A Laboratory Manual, $2^{nd}$ ed. 1989, CSH Press, Cold Spring Harbor, N.Y. and Ausubel et al., Current Protocols in Molecular Biology, Green Publishing Associates and Wiley Interscience, N.Y. (1989). Alternatively, the polynucleotides and vectors described herein can be reconstituted into liposomes for delivery to target cells. The vectors containing the polynucleotide described herein can be transferred into the host cell by well-known techniques, which vary depending on the type of cellular host. Preferably, the vector is a viral vector, more preferably it is a herpes simplex virus vector or a lentiviral vector. Vectors suitable for transfection of organotypic tissue cultures like brain slice cultures are described, e.g. in Lilley & Coffin (2003) and Lilley et al. (2001).

The term "recombinant" means, for example, that a polynucleotide sequence is made by an artificial combination of two otherwise separated segments of sequence, e.g., by chemical synthesis or by the manipulation of isolated polynucleotides by genetic engineering techniques.

The term "polynucleotide" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide" also includes DNAs or RNAs. It will be appreciated that a variety of modifications may be made to DNA and RNA that serve many useful purposes known to those of skill in the art. The term "polynucleotide" as it is employed herein embraces such chemically, enzymatically or metabolically modified forms of polynucleotides, as well as the chemical forms of DNA and RNA characteristic of viruses and cells, including, for example, simple and complex cells.

The organotypic tissue, e.g. a brain slice is usually transfected or transduced by contacting the tissue with the vector. Preferably, the transfection or transduction is performed in a manner such that pyramidal neurons are transfected or transduced. In addition, it is preferred to minimize vector consumption. For that purpose, a microdroplet is e.g. placed roughly onto the CA1 region of each individual slice. The microdroplet has a volume of from about 0.04 μl to about 0.2 μl, preferably of from about 0.05 μl to about 0.15 μl, more preferably of from about 0.06 μl to about 0.1 μl, even more preferably of from about 0.07 μl to about 0.09 μl, most preferably of about 0.08 μl. The microdroplet may be applied using a syringe, e.g. a 1 μl syringe, such as a 1 μl Hamilton syringe. This embodiment is preferably used for viral transduction of hippocampal slice cultures. It may be used, however, also for transfection or transduction of slices from other brain regions, e.g. cortex or midbrain or slices from retina explants.

Transformation of Non-Pathological Organotypic Tissue using APP:

In a specific embodiment, the transformation of non-pathological into pathological organotypic tissue comprises the step of contacting said organotypic tissue, e.g. a brain slice with β-amyloid precursor protein (β-APP) or a fragment or derivative or variant thereof. In another embodiment, the method further comprises the step of transfecting or transducing said at least one organotypic tissue with a recombinant vector comprising a polynucleotide encoding β-amyloid precursor protein or a fragment or derivative or variant thereof. The preferred fragment is the β-amyloid peptide $A\beta_{1-42}$. The β-amyloid peptide is derived from a larger Type I membrane spanning protein, β-APP, which has several alternatively spliced transcripts. The amino acid sequence of β-APP and $A\beta_{1-42}$ are described in. Kang J. et al., 1987; Knauer M. F et al., 1992; *Homo sapiens* APP (Gen-ID): NM 201414.

The term "fragment" as used herein is meant to comprise e.g. an alternatively spliced, or truncated, or otherwise cleaved transcription product or translation product. The term "derivative" as used herein refers to a mutant, or an RNA-edited, or a chemically modified, or otherwise altered transcription product, or to a mutant, or chemically modified, or otherwise altered translation product. For instance, a "derivative" may be generated by processes such as altered phosphorylation, or glycosylation, or, acetylation, or lipidation, or by altered signal peptide cleavage or other types of maturation cleavage. These processes may occur post-translationally.

Transformation of Non-Pathological Organotypic Tissue using Tau Protein:

The tau protein is preferably human tau protein. The amino acid sequence of wild type human tau protein is shown in SEQ ID NO:1. (*Homo sapiens* microtubule-associated protein tau (MAPT): NM 016834/NP_058518). The term "variant" as used herein refers to any polypeptide or protein, in reference to polypeptides and proteins disclosed in the present invention, in which one or more amino acids are added and/or substituted and/or deleted and/or inserted at the N-terminus, and/or the C-terminus, and/or within the native amino acid sequences of the native polypeptides or proteins of the present invention. Furthermore, the term "variant" includes any shorter or longer version of a polypeptide or protein. Variants comprise proteins and polypeptides which can be isolated from nature or be produced by recombinant and/or synthetic means. Native proteins or polypeptides refer to naturally-occurring truncated or secreted forms, naturally occurring variant forms (e.g. splice-variants) and naturally occurring allelic variants. The terms "variant" and "isoform" are used interchangeably herein. In one embodiment the tau protein or variant thereof according to the present application is capable of causing degeneration of dendrites and/or axons upon transduction of organotypic tissue e.g. brain slices with a vector comprising DNA encoding said tau protein.

Various isoforms of tau protein have been described. Known tau isoforms are summarized in Mandelkow & Mandelkow (1998) or Sergeant et al. (2005) Biochimica et Biophysica Acta 1739:179-197. The amino acid sequences of these tau variants/mutants and the nucleotide sequences encoding them are incorporated herein by reference. Preferred tau variants in accordance with this invention are tau mutants causing frontotemporal dementia and parkinsonism linked to chromosome 17 (FTDP-17). The most preferred tau variant in accordance with this invention has the mutation P301L which has been described to result in motor and behavioural deficits in transgenic mice, with age- and gene-dose-dependent development of NFTs. The amino acid sequence of the 0N4R isoform of human tau harbouring the P301L mutation comprises the amino acid sequence as shown in SEQ ID NO:3 (amino acid sequence P301L mutant: 275 VQIINKKLDLSNVQSKCGSKDNIKHV-LGGGS 305). The numbering of amino acids in the human tau sequences as used herein refers to the tau isoform having 441 amino acids which is shown in SEQ ID NO:2.

cDNA sequences encoding tau proteins are known in the art (e.g. Gen-ID NM016834). The skilled person can therefore easily manipulate the DNA by known techniques to provide polynucleotides that encode the desired tau protein or variant thereof.

Treatment of Organotypic Tissue with Test Compounds:

The method and device according to the present invention can be used for measuring intra- and extracellular physiological parameters and their alterations due to application of test compounds to the organotypic tissue explants. The impedance of the organotypic tissue can be analyzed during the treatment of the organotypic tissue with the test compounds or the impedance of the treated organotypic tissue can be compared with untreated organotypic tissues.

As used herein, the term "test compound" refers to any compound that is used for treating the organotypic tissue. The test compound can be a drug candidate and the effect of the drug candidate on pathological organotypic tissue (for e.g. determining the pharmaceutical activity of the test compound) or non-pathological organotypic tissue (for e.g. determining side effects of the test compound) is analyzed. Furthermore, the test compound can be a potential toxic compound and the effect of the test compound on non-pathological tissue is analyzed.

Test compounds (especially drug candidates) that are assayed in the above method can be randomly selected or rationally selected or designed. As used herein, a test compound is said to be randomly selected when the test compound is chosen randomly without considering the structure of other identified active test compounds. An example of randomly selected test compounds is the use a chemical library, a peptide combinatorial library, a growth broth of an organism, or a plant extract.

As used herein, a test compound (especially a drug candidate) is said to be rationally selected or designed when the test compound is chosen on a nonrandom basis. Rational selection can be based on the target of action or the structure of previously identified active test compounds. Specifically, test compounds can be rationally selected or rationally designed by utilizing the structure of test compounds that are presently being investigate for use in treating Alzheimer's disease.

The test compounds (especially drug candidates) are preferably: peptides, small molecules, and vitamin derivatives, as well as carbohydrates. The test compounds may be amino acids, viruses, nucleic acids, enzymes, natural or synthetic peptides or protein complexes, or fusion proteins, carbohydrates, biological active molecules, etc. They may also be antibodies, organic or inorganic molecules or compositions, drugs and any combinations of any of said agents above. They may be used for testing, for diagnostic or for therapeutic purposes. A skilled artisan can readily recognize that there is no limit as to the structural nature of the test compounds to be used in accordance with the present invention.

The potential toxic test compounds are preferably amino acids, peptides, proteins, enzymes, nucleic acids, carbohydrates, inorganic agents, organic agents, biological active molecules, quantum dots, nano-particles, pesticides, bacterias, fungis, yeasts, mycoplasms, body fluids etc. and any combination of these test compounds. Potential toxic substance are e.g. inorganic agents, organic agents, pesticides, bacterias, fungis, yeasts, mycoplasms, amino acids, peptides, proteins, enzymes, nucleic acids, carbohydrates, biological active molecules, quantum dots, nano-particles, body fluids etc and any combination of these test compounds.

At the commencement of an experiment, an organotypic tissue is typically transferred onto the liquid permeable membrane of the recording chamber of the device. The culture medium can either be present before the organotypic tissue is transferred to the recording chamber or the medium can be added after the organotypic tissue has been transferred to the recording chamber. Preferably, the transformation of the organotypic tissue or the treatment of the organotypic tissue with a test compound is carried out at culture day 3 or later, when the tissues are strongly attached to the liquid permeable membrane and the trauma of preparation has healed.

The transformation and treatment of the organotypic tissue can be carried out by adding the necessary substances to the media or the tissue. In general, a test compound or any other necessary substances will be first dissolved in appropriate vehicle, such as, but not limited to, DMSO, water, physiological saline, or media, to make a stock solution and then diluted into the media. A vehicle control test may be included when the present invention is used.

Preferably, a range of doses of test compounds (e.g. drug candidate or potential toxic compound) is tested. The range tested initially may be informed by prior knowledge of the effects of the test compound or closely related substances on purified proteins, cells in culture, or toxicity in other test systems. In the absence of such knowledge, the dose range is preferably from about 1 nM to about 100 µM. A skilled artisan can readily develop a testing range for any particular test compound or series of test compounds.

The test compound (e.g. drug candidate or potential toxic compound) is typically applied to the pathological organotypic tissue (obtained from individuals suffering from the concerned disease or transgenic animals or derived by transformation of non-pathological into pathological organotypic tissue) or to non-pathological tissue for about 4 hours to about 21 days, preferably from about 1 day to about 7 days. In the case of long term application, fresh medium containing the test compound can be applied periodically; more frequently if rapid loss of test compound due to chemical conversion or to metabolism is suspected.

Application of test compounds and medium exchange can be carried out manually or by an automated liquid handling system. For this purpose the lid of the multiwell plate can be transiently removed or liquid can be applied or exchanged through small microchannels integrated in the lid and membrane. The latter is needed for replacing medium or adding the test compound to the reservoir at the bottom side of the liquid permeable membrane.

Measuring Impedance:

In a first step organotypic tissues is generated as described herein. Preferably the organotypic tissue is obtained from brain slices or retinal explants, further preferred from brain slices, more preferred from the hippocampus. The organotypic tissue(s) is/are transferred onto the liquid permeable membrane(s) in the recording chamber(s). The organotypic tissues can be pathological or non-pathological as described above. In the following, we will use the expression "organotypic tissues", wherein it is understood that also only one organotypic tissue can be used for measuring impedance. Organotypic tissue cultures are maintained on top of the biocompatible liquid permeable membranes of the recording chambers. The organotypic tissues are then cultured in the recording chambers according to well-known methods and e.g. described in example 1. Preferably, first impedance measurements are performed at culture day 3 or later, when the tissues are strongly attached to the liquid permeable membrane and the trauma of preparation has healed.

In an optional second step, the non-pathological (healthy) organotypic tissue is transferred into pathological tissue in different ways as described herein. The second step is not necessary if either pathological tissue is directly used, or if non-pathological tissue is treated with test compounds.

In an optional third step, application of test compounds to the organotypic tissues can be performed.

Impedance recording can be carried out according to any known method for measuring impedance, preferably according to the following three procedures: For transient indirect electrode contact impedance recording (TIECIR) the organotypic tissues are cultured with a small volume of medium (bottom side of the organotypic tissue has contact to the culture medium). During impedance measurement the recording chamber is transiently filled with culture medium to cover the top electrode(s) and to guarantee the completion of the electric circuit. Thereafter, culture medium is immediately removed up to the original level (FIG. 5A). The procedure can be performed several times.

For permanent indirect electrode contact recording (PIECIR) the procedure is similar to TIECIR with the exception that the medium is not removed and remains within the recording chamber for at least 3 days (FIG. 5B).

For transient direct electrode contact recording (TDECIR) the top electrode is movable and can be directly placed onto the organotypic tissue during impedance measurement (FIG. 5C). After recording the electrode can be traced back and re-positioned for subsequent and continuous recording.

The TIECIR and TDECIR are the preferred methods since they ensure air exchange on the upper surface of the biological sample which in turn is essential for maintaining viability and morphology of the organotypic tissues.

During the above described steps, monitoring of impedance changes at multiple frequencies can be carried out for preferably up to 8 weeks. In this way, alteration in intracellular compartments, extracellular compartments, cell membranes, proliferation, apoptosis, differentiation, migration, phosphorylation, dephosphorylation, formation and dissolving of tangle and plaque can be monitored. All experiments may be performed at least in triplicate to carry out appropriate statistical analysis. To calculate the E50 value of the test substance various concentrations can be applied to the organotypic tissues.

Cellular parameters of the organotypic tissue (pathological or non-pathological, optionally treated with test compounds) are detected by recording of frequency dependent impedance magnitudes and phase angles. Subsequent and continuous impedance recordings at a single frequency or multiple frequencies provide valuable information about cellular properties. For measuring impedance changes in organotypic tissues, an alternate electrical current or voltage (1 mV-100 mV) at a frequency range of 1 Hz to 100 MHz are applied to the said electrodes. Cellular parameters can be detected by recording the frequency-dependent changes in resistance and reactance of organotypic tissues located between at least one pair of electrodes (top and bottom electrodes). Impedance changes can be analyzed by measuring the resistant, reactance, capacitive reactance, inductive reactance and any value that can be calculated by using a combination of these parameters.

Changes in impedance can be caused by alterations of intracellular or extracellular processes that have been induced by application of test compounds, transformation of non-pathological into pathological form etc. or by deprivation of essential components of the culture medium and reducing atmosphere.

When recording impedance, preferably the impedance magnitude, phase angle, and normalized impedance are plotted against the frequency and time (e.g. x-axis=time; y-axis=impedance magnitude (or phase angle, or normalized impedance); z-axis=frequency). The impedance measurements on pathological and non-pathological organotypic cultures can be continuously performed.

In order to minimize time consuming controlling of all individual electrodes, the alternate current or voltage is preferably applied to all bottom electrodes. If a multiwell format is used, preferably each of the 6-384 top electrodes (depending on the used multiwell format) can be individually multiplexed for impedance recording. The time needed for the impedance measurement can be reduced further by using a multi sinus input signal that allows parallel impedance measurement at different frequencies and that can be selected for the analysis of distinct cellular parameters.

Furthermore, the bottom electrodes are separated by a stripe-shaped ground electrode to minimize parasitic interferences (increasing signal-to-noise ratio) as described above. The microelectrode-based multi site recording of up to 384 electrodes can be realized by 2- or 4-point measurements. To enable a fast and precise data read out, the alternating current is applied simultaneously to all bottom electrodes (or subsequently), whereby the data read out is achieved by multiplexing individually controllable top electrodes (may be integrated in the lid of the multiwell plate). The impedance recording is performed in a frequency range of 1 Hz to 100 MHz with a maximal amplitude of the alternating current of 1 to 100 mV to prevent non-linear effects and to reduce thermal interferences. Cellular parameters are detected by the recording of the frequency dependent impedance magnitude and phase angle. Both values can be normalized to control experiments and provide information about intra- and extracellular modifications.

Preferably, the bottom electrodes (for reference) have a stable and fixed electrode potential whereas the top electrodes (for measuring) are individually or simultaneously addressable via the multiplexer. In an alternative approach the substrate integrated electrodes at the bottom of the recording chamber can serve as measuring electrodes by using an multiplexer, wherein the top electrodes in the top chamber can act as reference electrodes.

Method for Analyzing Impedance During Transformation of Organotypic Tissue:

Based on the non-invasive and free-free measuring principle of impedance spectroscopy continuous and repeated recordings of the same tissue sample before, during and after disease-(pathology) inducing substances can be performed. The preparation of organotypic tissue and the transformation of the non-pathological form into the pathological form during culturing of the organotypic tissue in the recording chamber is described above.

In one embodiment of the invention, the transformation of non-pathological into pathological organotypic tissue can be analyzed by measuring the impedance of the organotypic tissue before, during and after the transformation of the organotypic tissue, preferably by using the device according to the present invention.

The onset and progression of pathological mechanisms on organotypic tissues can be analyzed by continuous measurement of impedance or by measuring impedance in time intervals (e.g. every 2 hours).

After induction of pathological processes, impedance measurements over several weeks may provide valuable information about cellular alteration that are directly associated with diseases like AD. Occurring alterations in impedance amplitude and phase angle at various time points can be related to the initial cellular situation and thereby provide information about cellular parameters involved in the etiology of the diseases.

In one preferred embodiment, the basic pathological mechanisms after induction of neurodegenerative disease (preferably AD) relevant mechanisms on hippocampal slice cultures are analyzed. However, organotypic cultures can be generated from any other part of the brain or retina. Moreover, organotypic tissue cultures can be produced from prenatal (embryonic), postnatal and adult animals of non-vertebrate, vertebrate, mammalian, including primate species and human.

Method for Analyzing the Effect of Test Compounds on Organotypic Tissue:

The method according to the present invention can be used to analyze the effect of test compounds on organotypic tissue. In order to screen drug candidates, the impedance of the pathological organotypic tissue is preferably measured before, during and after treatment of the tissue with the test compounds. In this embodiment of the invention, the pathological organotypic tissue can be obtained by any method as described herein. It is also possible to analyze the effect of a drug candidate on non-pathological tissue.

Furthermore, the method according to the present invention can be used to analyze the effect of potential toxic compounds on non-pathological tissue. In this case, non-pathological organotypic tissue is treated with the test compounds and the impedance of the tissue is preferably measured before, during and after this treatment. According to all methods of the present invention, it is also possible to compare the impedance of the treated organotypic tissue with another non treated organotypic tissue.

After isolation of pathological or non-pathological slice or explant cultures and cultivation on biocompatible liquid permeable membranes of the recording chambers, a positive or negative effect of the test compounds is identified by alterations of the impedance spectra. The impedance of the organotypic tissue can be measured before, during and after application of test compounds (preferably up to 8 weeks) or by comparing treated with non-treated cultures. As described above, the impedance can be measured continuously or at selected different time points for data read out.

Subsequent and continuous impedance recordings at multiple frequencies (1 Hz-100 MHz) provide valuable information about the efficiency and safety (side effects) of the test compounds.

Pathological organotypic tissues (pathological slice or explant cultures) for impedance measurement can be obtained directly from transgenic animals carrying mutations relevant for any neurodegenerative disease (e.g. Parkinson's disease, Huntington's disease amyotrophic lateral sclerosis, prion diseases, Pick's disease, fronto-temporal dementia, progressive nuclear palsy, corticobasal degeneration, multiple system atrophy, mild-cognitive impairment, ischemic stroke, multiple sclerosis, motor neuron diseases, nerve injury and repair, age related macular degenerations, rod-cone dystrophy, cone-rod dystrophy, retinitis pigmentosa, glaucoma, and other retina associated degenerations), preferably AD. After isolation from transgenic animals, pathological slice or explant cultures can be cultured and maintained within the recording chambers.

In an alternative embodiment of the invention, general toxicity of substances can be analyzed by using non-neuronal organotypic tissues derived from any part of the individual.

By using already existing pathological animal models for organotypic cultures, identification and characterization of test compounds can be directly performed without previous transformation of non-pathological into pathological organotypic tissues.

Preferably, test compounds include drugs, liquids, water, amino acids, peptides, proteins, enzymes, nucleic acids, carbohydrates, inorganic agents, organic agents, biological active molecules, quantum dots, nano-particles, pesticides, bacterias, fungis, yeasts, mycoplasms, body fluids and any combination of them. In one embodiment, food and environmental compounds are analyzed with respect to their effect on cellular changes by impedance measurement. The invention is preferably used to screen substances for neurotoxicity. Any potential harmful substance or substances with a strong suspicion (substances derived from environmental or indoor pollution) can be monitored by applying these substances to the non-pathological organotypic tissues. Toxicity can be analyzed by measuring the impedance changes before, during and after application or by comparing treated with non-treated organotypic cultures. Subsequent and continuous impedance recordings at multiple frequencies (1 Hz-100 MHz) can provide valuable information about toxicity.

The preferred organotypic tissues for determining toxic effects of test compounds may be obtained from liver, heart, spleen, gut, pancreas, kidney, skin, skeleton muscle and any other organ or tissue.

The method according to the invention is also suitable for identifying test compounds that counteract to different pathological mechanisms related to neurodegenerative diseases such as Parkinson's disease, Huntington's disease amyotrophic lateral sclerosis, prion diseases, Pick's disease, fronto-temporal dementia, progressive nuclear palsy, corticobasal degeneration, multiple system atrophy, mild-cognitive impairment, ischemic stroke, multiple sclerosis, motor neuron diseases, nerve injury and repair, age related macular degenerations, rod-cone dystrophy, cone-rod dystrophy, retinitis pigmentosa, glaucoma, and other retina associated degenerations), preferably to Alzheimer disease (AD).

DETAILED DESCRIPTION OF THE FIGURES

FIG. 1 is a schematic representation of a single recording chamber 29. The recording chamber 29 comprises a substrate 25 onto which the bottom electrode 26 and conductors (not shown) are spotted. On top of the substrate 25 is a passivation layer 27. The (biocompatible) liquid permeable membrane 28 divides the recording chamber 29 into a top chamber 30 and a bottom chamber 31. During the experiment, at least the bottom chamber 31 contains a culture medium 32. The culture medium 32 is in contact at least with parts of the organotypic tissue 35, which is cultured on the liquid permeable membrane 28. The lid 36 prevents evaporation of the medium and serves as device for fixing the flexible top electrode 34 and conductor board (not shown). The latter may acts as basis for the multiplexer board (not shown). The lid has at least one microchannel 37 of 0.5 mm to 1 cm diameter and the liquid permeable membrane 28 has an opening 33 to fill or to exchange medium, and to apply test substances or any other necessary substances. Medium exchange and application of test compounds can be performed manually or by an automated liquid handling system that is integrated in a $CO_2$ incubator.

FIG. 2 shows a schematic representation of the invention comprising a computer 1, an impedance/gain-phase analyzer 2, a multiplexer 3, a $CO_2$ incubator 4, and a multiwell frame 5 containing the biological samples 35. The computer 1 includes software tools for controlling the impedance/gain-phase analyzer 2, the multiplexer 3 and for acquisition and analyses of impedance data. The impedance analyzer 2 is connected to the electrodes (not shown) via a multiplexer 3. The multiplexer 3 is needed for applying an alternate currents or voltages simultaneously or individually to the electrodes of the multiwell format. For measuring impedance changes of organotypic tissues 35 an alternate electrical current or voltage (1 mV-100 mV) at a frequency range of 1 Hz to 100 MHz are applied to the said electrodes. Cellular parameters can be detected by recording the changes in resistance and reactance of tissues located between at least one pair of electrodes. To achieve stable and reproducible impedance recordings the tissues are preferentially cultured and maintained in a $CO_2$ incubator in a humidified atmosphere of 5% $CO_2$, 95% air and 37° C. For certain tissues or to induce pathological (e.g. ischemic) conditions culture parameters can be varied (0-50% $O_2$, 0-50% $CO_2$, 33-42° C.). Within the $CO_2$ incubator an automated liquid handling system can be implemented.

FIG. 3 illustrates a multiwell format comprising a lid 36 that may contain an implemented multiplexer board 8, a multiwell frame 9 that can consist of different formats (6-, 12-, 24-, 48-, 96-, 192-, 384-wells), a substrate 25 with integrated electrodes and conductors that can be linked via connection pads 22 placed at the periphery of 25. The electrodes, conductors and connection pads 22 are integrated in the substrate 25. The connection pads 22 allow to connect the electrodes to the multiplexer, computer etc.

Figure 4:
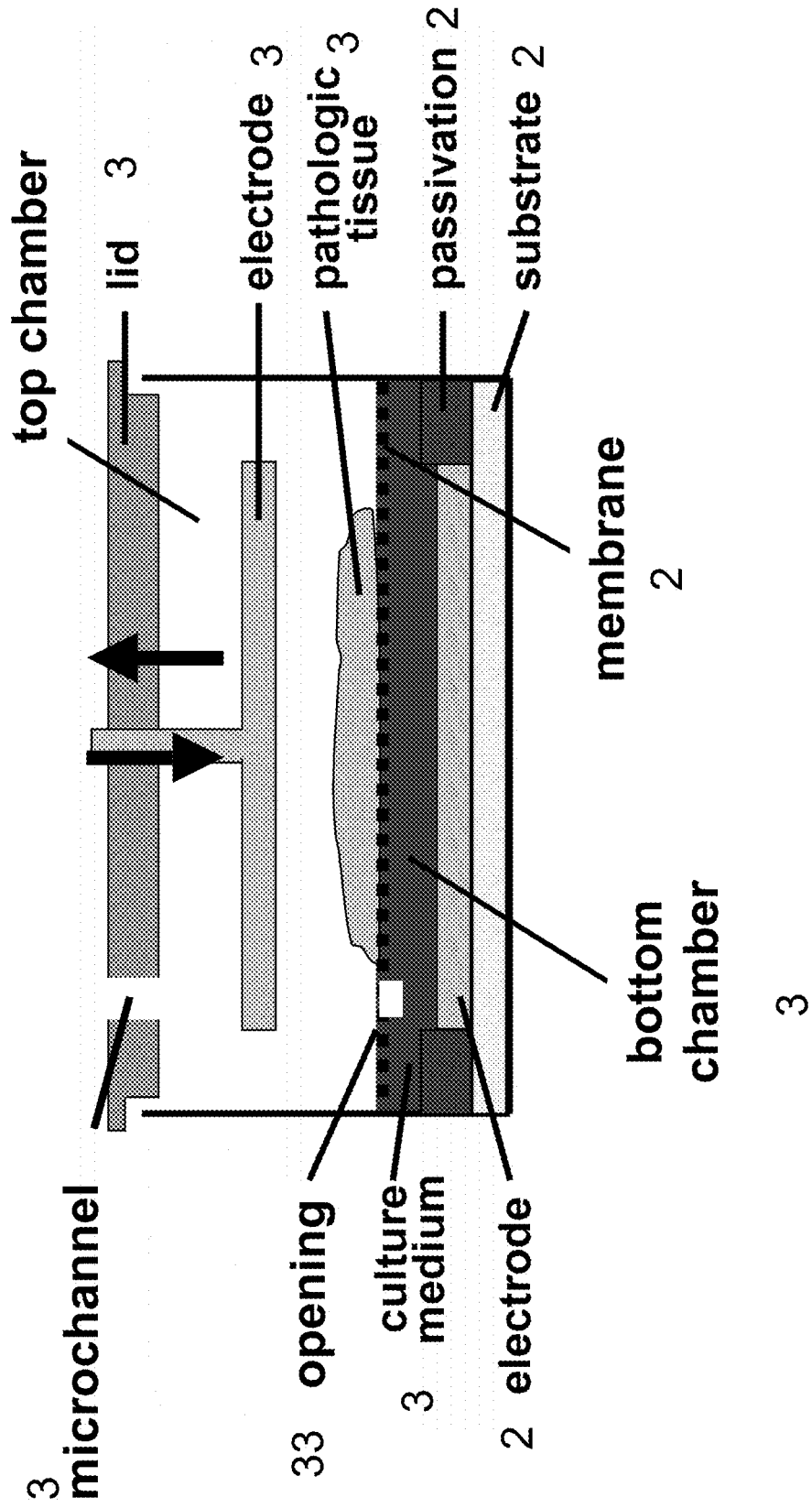
FIG. 4 illustrates a schematical description of a 384 wells multiwell frame 5 with an (biocompatible) liquid permeable membrane 28 for cultivation of organotypic tissues 35. The liquid permeable membrane 28 extends over all recording chambers 29. Each recording chamber 29 contains a top electrode 34, a top chamber 30, a bottom chamber 31, ground electrode 18 and bottom electrodes 26. The substrate 25 (e.g. made of glass) represents the bottom of all recording chambers 29. The substrate 25 comprises a passivation layer 27, connection pads 22 (which are connected to the bottom electrodes 26), and ground pads 11 (which are connected to the ground electrodes 18). On top of the recording chambers 29 is a lid-integrated multiplexer board 8.

FIG. 4 illustrates a more detailed schematic representation of a multiwell device according to the invention. Herein, the tissue sample 35 can be cultured and maintained on a biocompatible membrane 28 of e.g. a 6-, 12-, 24-, 48-, 96-, 192-, or 384-wells plate. The impedance changes are measured between or among at least one top electrode 34 positioned in the top chamber 30 and at least one bottom electrode 26 that is implemented in the bottom chamber 31 of each recording chamber 29. The stripe-shaped ground electrode 18 is localized in between the bottom electrodes 26 and is suited to minimise parasitic interferences (increasing signal-to-noise ratio). The substrate 25 also contains conductors 19, wherein means 26, 18 and 19 can be sputtered onto the substrate 25 (e.g. made from glass). Isolation of 26, 18, and 19 can be achieved by using an appropriate passivation layer 27. An external connection pad 22 and a ground pad 11 provide contact to the impedance/gain-phase analyzer. In this case, the bottom electrode 26 (for reference) has a stable and fix electrode potential whereas the top electrodes 34 (for measuring) are individually or simultaneously addressable via the lid-integrated multiplexer board 8. In an alternative approach the substrate integrated electrodes 26 at the bottom of the multiwell plate can serve as measuring electrodes by using an external multiplexer, whereas the top electrodes 34 in the top chamber 30 can act as reference electrodes.

FIGS. 5-A to 5-C show the three different ways for measuring impedance using the method and/or the device according to the present invention. FIG. 5A shows the transient indirect electrode contact impedance recording (TIECIR). For TIECIR, tissues are cultured in the presence of a small volume of medium (bottom side of tissue has contact to the medium). During impedance measurements the recording chamber is transiently filled with medium to cover the top electrode and to guarantee the completion of the impedance circuit. Thereafter, the excess of medium is removed up to the original medium level. This procedure can be performed several times without influencing viability and morphology.

FIG. 5B depicts the permanent indirect electrode contact impedance recording (PIECIR). PIECIR is comparable with TIECIR. However, for PIECIR the medium is not removed and remains within the recording chamber for several days. This method is well-suited to induce a pathological situation since neuronal ex vivo tissues such as brain slices or retinal explants show an ischemic behaviour if they are losing contact to the air phase.

FIG. 5C shows the transient direct electrode contact impedance recording (TDECIR). For TDECIR, the top electrode is movable and can be directly placed onto the ex vivo tissue during impedance measurement. After recording, the electrode can be traced back to provide the upper tissue surface with air. In a new cycle the measuring electrode can be placed again onto the tissue and impedance recordings can be performed again. The process can be repeated at least 10 times a day without influencing the quality of the tissue. The contact time between electrode and tissue during impedance measurement may not exceed 60 minutes. In this manner, the tissue can be monitored for 6-8 weeks.

FIG. 6A to 6I illustrates organotypic hippocampal slice cultures that have been obtained from 8-9 day old rats and subsequently cultured on a biocompatible liquid permeable membrane. After 7 days in vitro, organotypic slice cultures were exposed to repeated medium overflow for 15 minutes (6-A, 6-D, 6-G) or 30 minutes (6-B, 6-E, 6-F) to simulate conditions that can be found during TIECIR, PIECIR, and TDECIR (compare FIG. 5A to 5C). The procedure was carried out over a period of four days. Thereafter, viability was tested by diamino fluorescein diacetat (6-D, 6-E, 6-F), while cell death was analyzed by propidium iodide (6-G, 6-H, 6-I). Comparison of control cultures (6-C, 6-F, 6-I) with cultures that were not covered with medium (6-A to 6-H) showed no significant changes in viability and cell death. This means, that all three procedures needed for TIECIR, PIECIR, and TDECIR) are well-suited for culturing and recording of organotypic tissues.

For the generation of retinal explant cultures, we used retina of 10-day old chicken embryos. The retina was placed either in toto or in pieces on the top of a polycarbonate membrane (3 µm pore size). The culture period can be extended up to 6 weeks. The medium is exclusively localized in the bottom compartment and was changed every two days. Similar to hippocampal slice cultures retinal explants showed no increase in cell death.

Figure 7B:
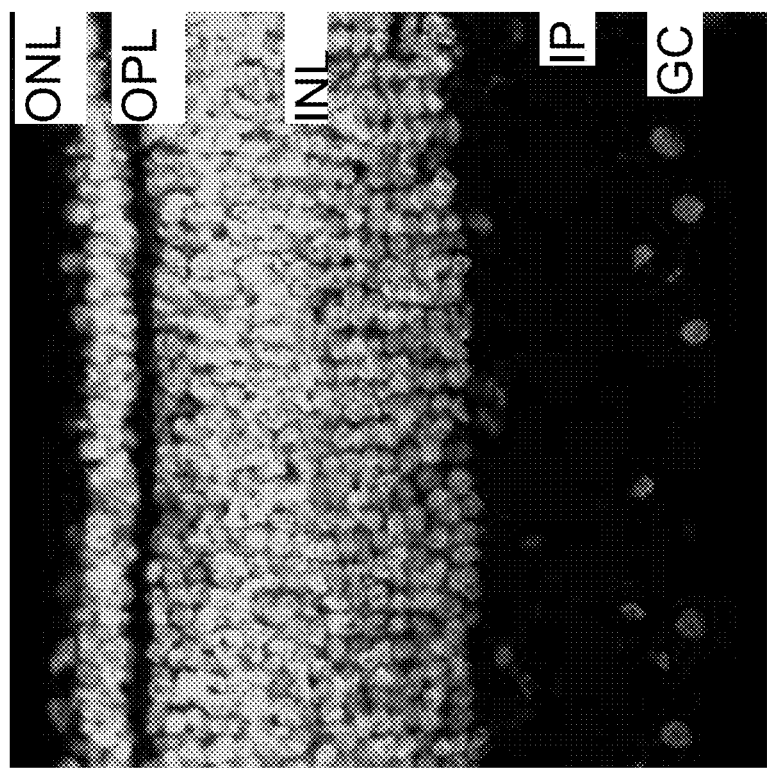
FIGS. 7A and 7B show retinal explants isolated from 10-day old chicken embryos that were cultured for 10 days on a membrane of a 6-well recording chamber (FIG. 7-A). An in vivo retina of embryonic stage 20 is shown in FIG. 7-B. Abbreviations: ONL, outer nuclear layer; OPL, outer plexiform layer; INL, inner nuclear layer; IPL, inner plexiform layer; GCL, ganglion cell layer.
Figure 7A:
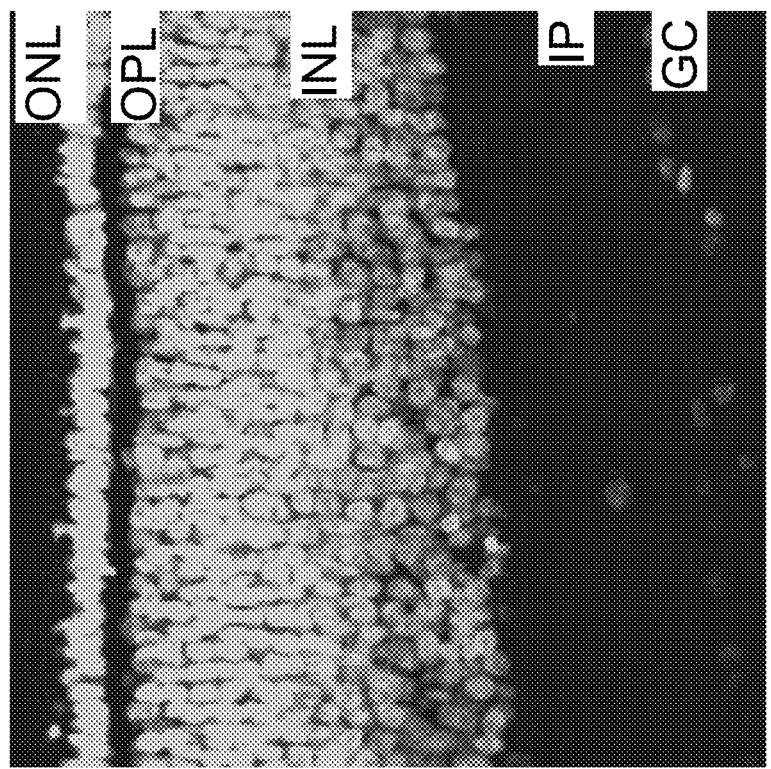

FIGS. 7A and 7B show retinal explants isolated from 10 day old chicken embryos that have been cultured for 10 days on a membrane of a 6-well recording chamber. The retinal explants were harvested, fixed and cut into 20 µm thick sections with a cryotome. To visualise the quality of the morphology and lamination of retinal layers, sections were stained with cytox green, which specifically stains cell nuclei (FIG. 7A, 7B). By comparison of 20 days old organotypic cultures (FIG. 7A) with in vivo retina of embryonic stage 20 (FIG. 7B), we found no significant differences.

Figure 8A:
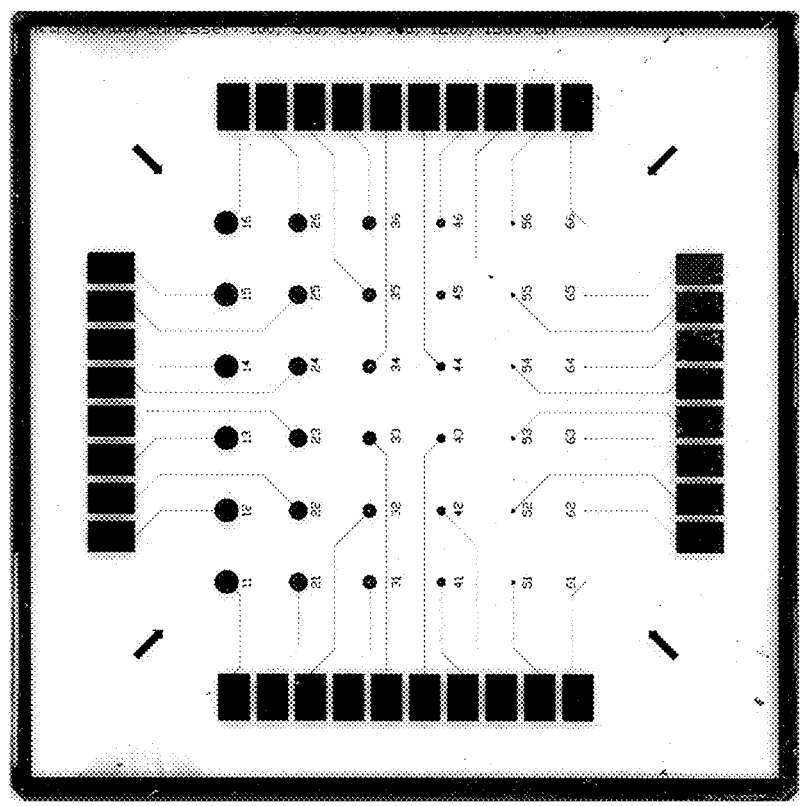
FIGS. 8A and 8B illustrate a substrate 25 for the evaluation of the optimal size of the bottom electrodes 26 for the impedance-based multiwell method. Bottom electrodes 26 (made of gold) of different sizes are sputtered onto a borosilicate glass substrate 25 (FIG. 8-A). For evaluation of the bottom electrodes 26, a 384 multiwell frame 5 (defining the recording chambers 29) was glued onto the substrate 25 (FIG. 8-B).
Figure 8B:
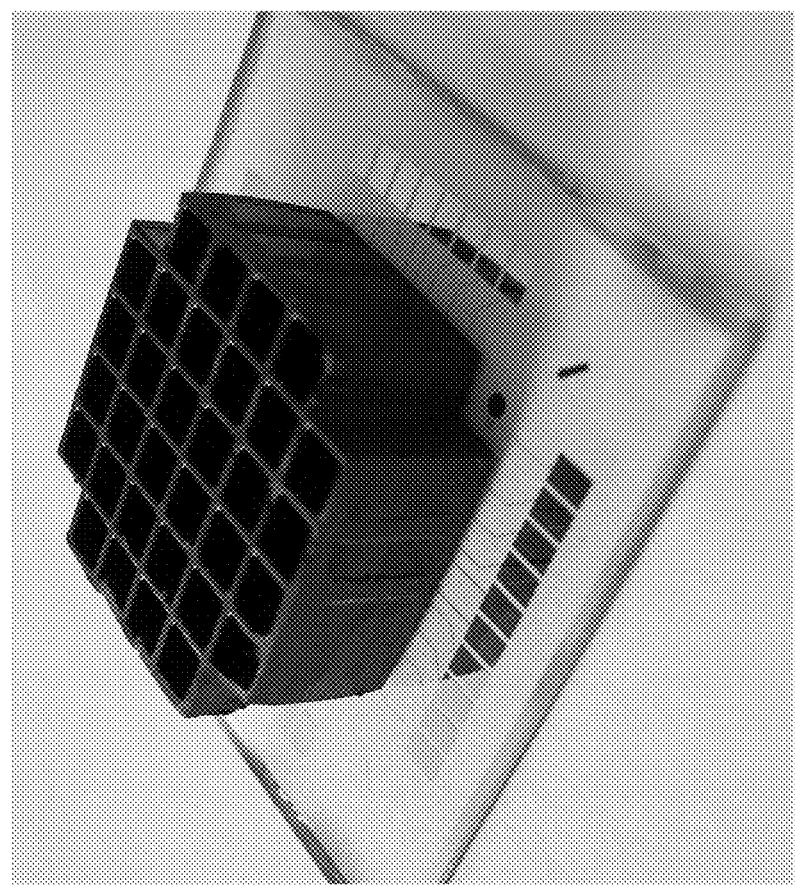

FIGS. 8A and 8B illustrate the evaluation of the optimal electrode size for the impedance-based multi-well assay. Borosilicate glasses were used as substrate (FIG. 8A) for fabrication of the sensor chip.

Figure 9:
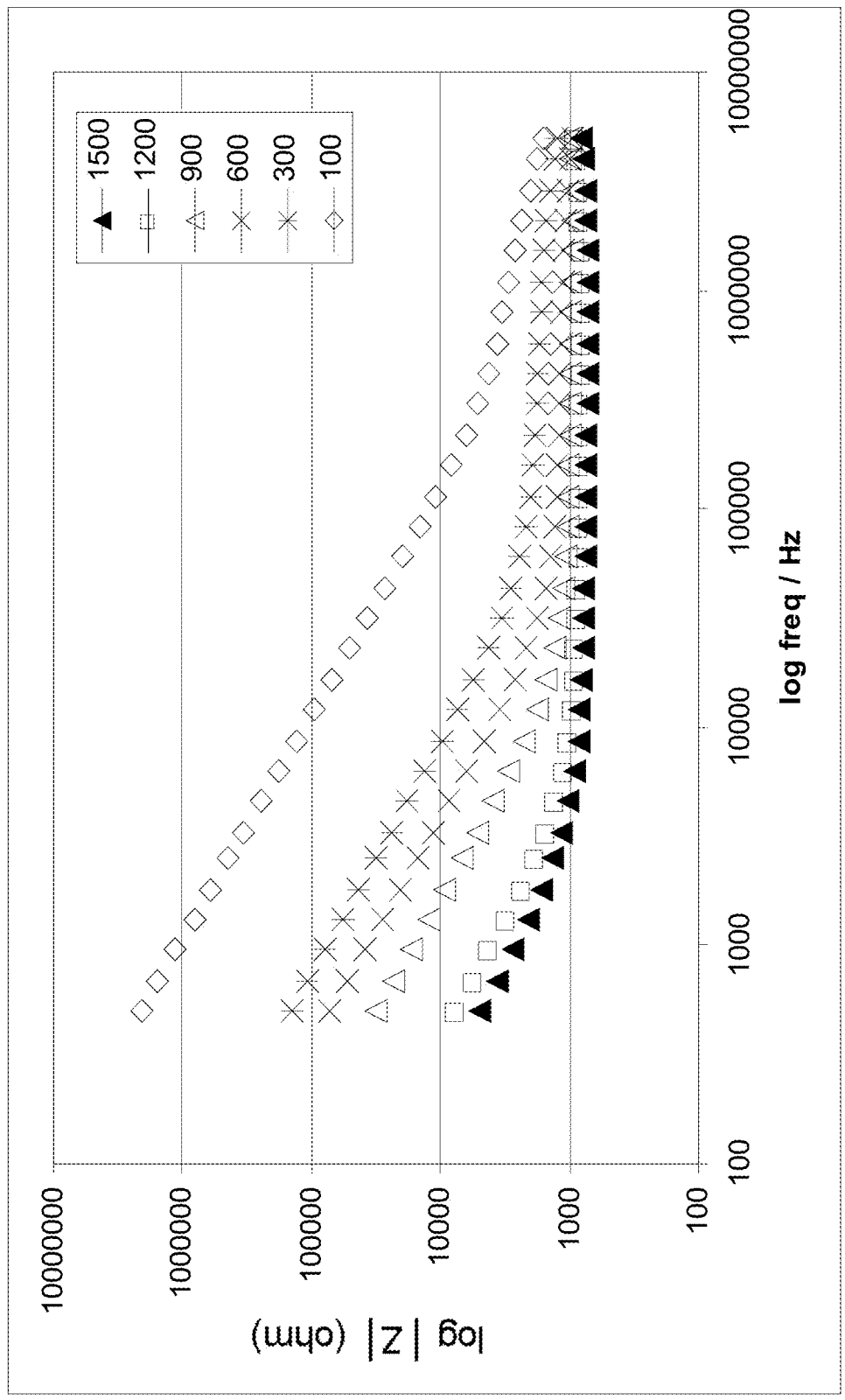
FIG. 9 depicts the impedance of the bottom electrodes 26 with respect to the size of the electrodes 26. A 6×6 frame with dimensions of a 384 multiwell plate was glued onto the glass substrate and filled with 80 µl phosphate buffered saline (PBS). The impedance was recorded in a frequency range of 100 Hz to 10 MHz.

FIG. 9 depict the impedance of the bottom electrodes 26 with respect to the size of the electrodes 26. To determine the electrode impedance in respect to the electrode size, a 6×6 frame of a 384 well plate was glued onto the glass substrate and filled with 80 µl phosphate buffered saline (PBS). The impedance was recorded in a frequency range of 100 Hz to 10 MHz by applying a voltage of 10 mV across the substrate integrated electrode and a top electrode that has been dipped from the top into the PBS. As expected the impedance magnitude decreased as the diameter of the electrodes increased.

Figure 10:
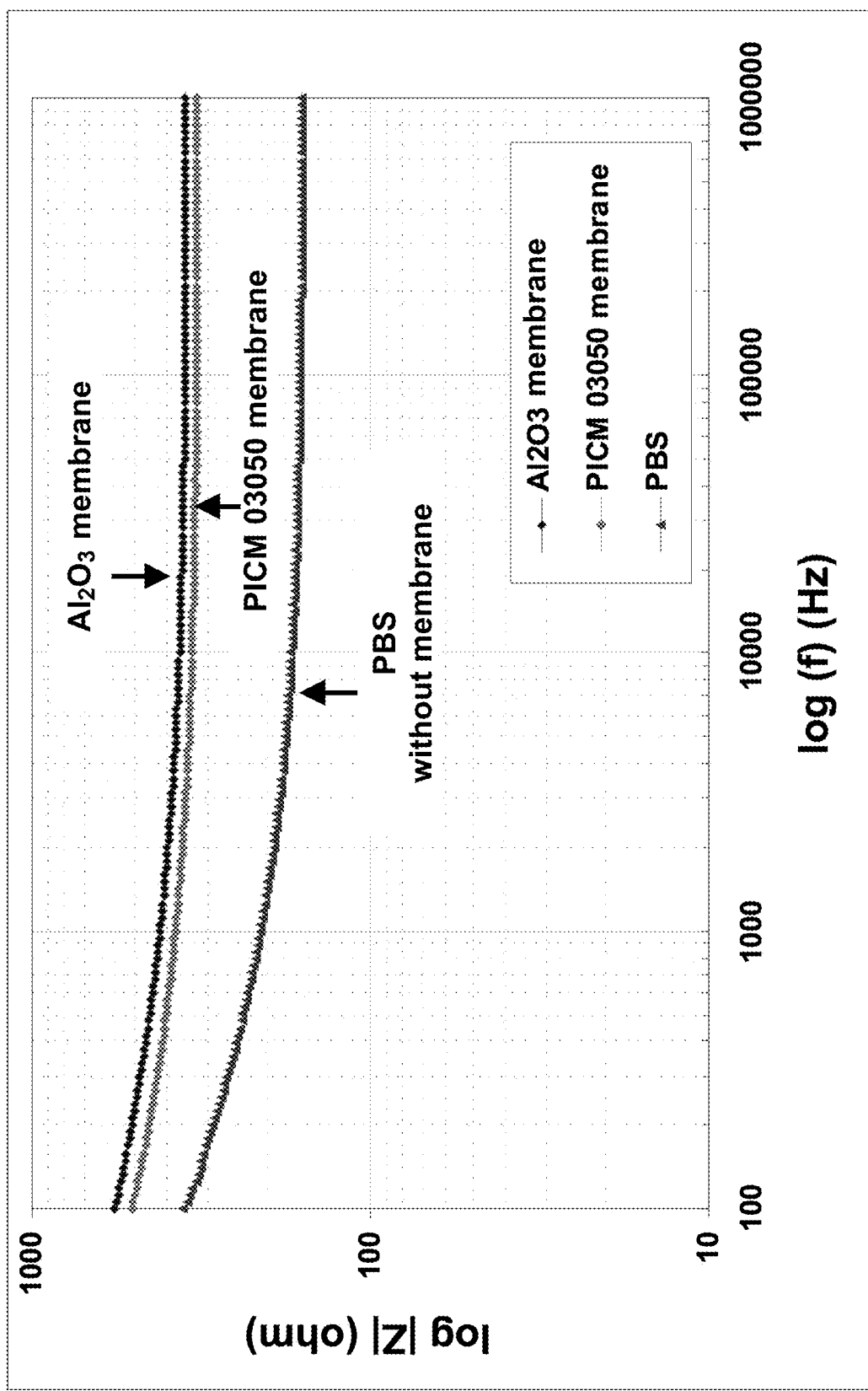
FIG. 10 illustrates the impedance of (biocompatible) liquid permeable membranes suited for cultivation of organotypic tissues. The impedance amplitude was recorded in a frequency range of 100 Hz to 10 MHz. The impedance spectra of an aluminiumoxyd membrane from TPP Switzerland (pore size 0.02 µm) and a PICM 03050 membrane from Millipore (pore size 0.4) is shown. Impedance measurement without membrane.

FIG. 10 illustrates the impedance of membranes within the recording chamber. The impedance was recorded in a frequency range of 100 Hz to 1 MHz by applying a voltage current of 10 mV across the substrate integrated electrode and a top electrode that has been dipped from the top into the PBS. Two membranes of different materials and pore sizes were tested. The impedance spectra of an aluminiumoxyd membrane from TPP Switzerland (pore size 0.02 µm) and a PICM 03050 membrane from Millipore (pore size 0.4) is shown in FIG. 10. Both types of membranes have similar impedance magnitudes. Surprisingly, impedance measurements that were carried out only in PBS (without membranes) were slightly lower than those performed with membranes.

Figure 11:
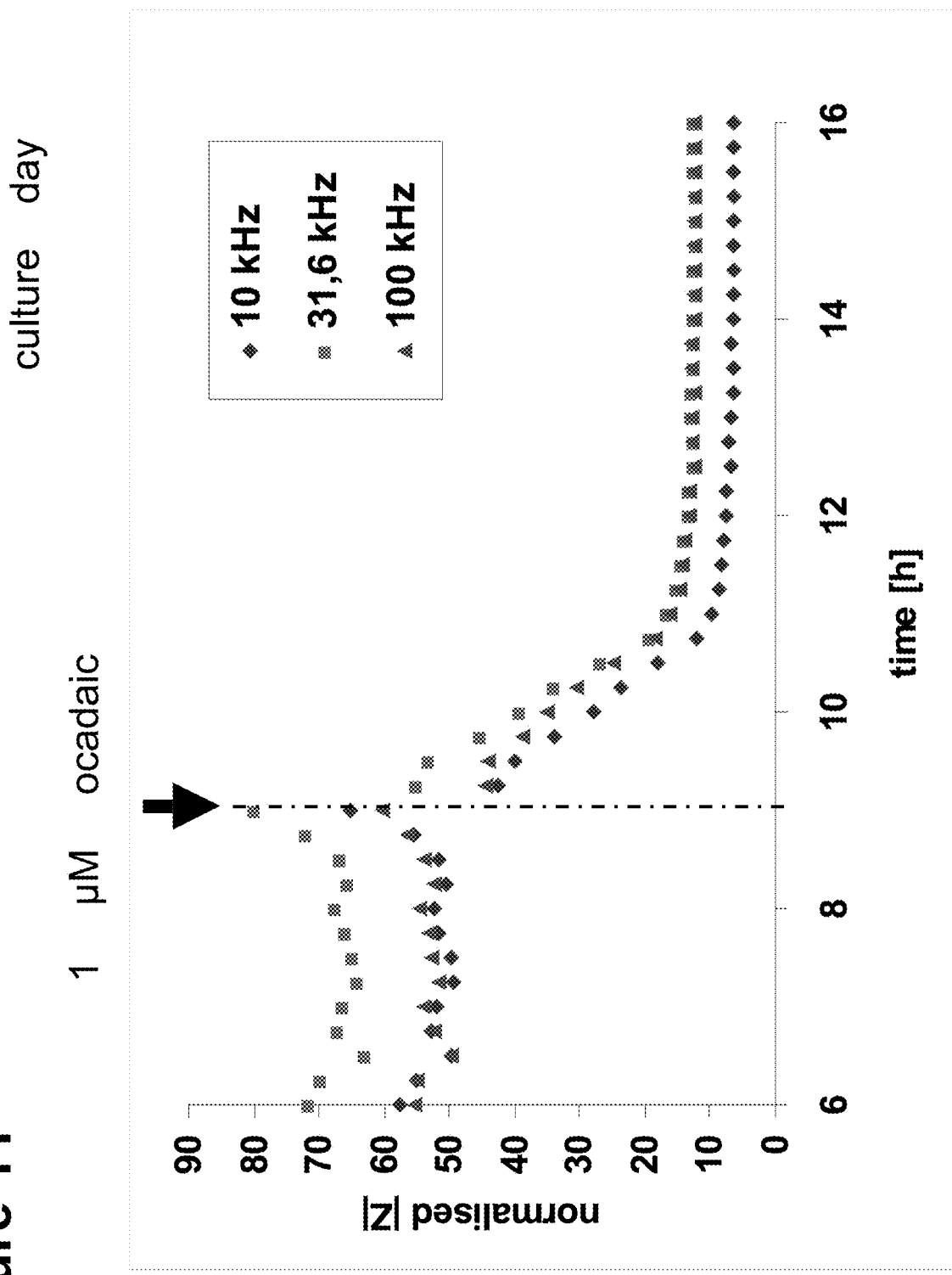
FIG. 11 shows the measuring of impedance caused by tau-hyperphosphorylation of hippocampal slices as described in example 2.

FIG. 11 shows the measuring of impedance caused by tau-hyperphosphorylation of hippocampal slices as described in example 2. Six to eight hippocampal slices of 400 µm thickness were placed on aluminiumoxyd membranes (0.02 µm pore size) of a 6-well recording chamber.

EXAMPLES

Example 1—Preparation of a Substrate with Integrated Electrodes

Borosilicate glasses were used as substrate (FIG. 8A) for fabrication of the sensor chip. The substrates were washed thoroughly with a lint free cotton wool tip subsequently in water, acetone, propanol and water followed by incubation in a solution of 96% sulphuric acid in 30% hydrogen peroxide and two wash steps in a water bath cascade. The substrate was centrifuged and dried on a hot plate. Substrate coating was performed by centrifugation. For this purpose 500 µl of positive photo resist was applied in the centre of the substrate. The subsequent centrifugation dispersed the lacquer equally over the substrate yielding layer of a thickness of 3 µm. The positive photo resist coat was dried for a minimum of 5 minutes on a hot plate. By means of a chrome mask the brim of the substrate radiated by UV-light for 10 seconds. Next the substrate was put into developer to remove the lacquer, followed by a washing step in a water bath cascade and centrifugation. The pattern for the electrodes and interconnects was removed from the lacquer coat with another chrome mask repeating the steps before and drying on a hot plate. The substrate was sputtered with a 100 nm thick layer of gold to deposit electrodes and interconnects. Next the substrate was placed in acetone and rinsed in water to remove the polymerized positive-photo resist, getting a substrate with gold electrodes and interconnects. The substrate was dried with a stream of N2 and placed on a hot plate. The passivation was performed to isolate the interconnects and embed the electrodes. Therefore, 1 ml of SU-8 was applied in the centre of the substrate and centrifuged to dispense the lacquer to 1.5 µm thick film followed by drying on a hot plate. With a folia mask covering the electrodes, the passivation-layer was radiated with UV-light for 20 seconds. Then the substrate was incubated on a hot plate for 1 minutes at 60° C., 1 minutes 95° C. and put into beaker with photo-developer for 1 minutes. The chip was washed in propanol to remove all traces above the electrodes of the negative photo resist layer. Finally, the chip was dried under a stream of nitrogen and evaluated microscopically. Gold electrodes electrodes have diameters of 100, 300, 600, 900, 1200, and 1500 µm while interconnects have a width of 10 µm. The resulting substrate can be used as the bottom of the multiwell frame.

Example 2—Induction of Pathological Tau-Hyperphosphorylation and Impedance Measurement The impedance changes caused by tau-hyperphosphorylation (FIG. 11) of hippocampal slices that were prepared from 8-9 day old rats were measured using the device according to the present invention. Six to eight hippocampal slices of 400 µm thickness were places on a aluminiumoxyd membrane (0.02 µm pore size) of a 6-well recording chamber and cultured for 7 days in 50% minimum essential media, 25% Hank's media, and 25% horse serum supplemented with L-glutamine and antibiotics. Impedance recording was performed by using a Agilent 4294A impedance analyser (Agilent Technologies Deutschland GmbH, Germany) in combination with a multiplexer (NI-SCXI-1153, National Instruments, USA).

24 hours before impedance measurement was carried out, medium replaced by fresh culture medium. The impedance was recorded in a frequency range of 100 Hz to 1 MHz by applying a voltage of 10 mV across a large top electrode and 60 substrate integrated bottom electrodes of 30 µm in diameter.

For measuring hippocampal slice cultures, the TIECIR method was used. Organotypic slice cultures were transiently covered with medium during impedance measurement, which usually takes less than 30 seconds for a single bottom electrode. If all 60 substrate integrated electrodes were used for recording, the complete measurement takes approximately 20 min for a frequency range of 100 Hz to 1 MHz (with 5 measuring points per frequency). For better illustration, the impedance spectra in FIG. 11 shows only three frequencies that were recorded over 16 hours by TIECIR with a single top and bottom electrode. The normalized impedance (normalized against non-covered membrane) of hippocampal slice cultures was stable for 9 hours. After application of 1 µM ocadaic acid, which induces tau-hyperphosphorylation, impedance was significantly dropped down to 10% and remained small within the next seven hours. For repeated impedance measurements by TIECIR the complete medium was exchange and fresh ocadaic acid has been applied.

---

What is claimed:

1. A method for measuring impedance in an organotypic tissue sample, said method comprising the steps of:
   i) providing a device comprising: (a) one or more recording chambers, each of which comprises a liquid permeable membrane capable of supporting the positioning and growth of an organotypic tissue sample, wherein said liquid permeable membrane divides each recording chamber into a top chamber and a bottom chamber and defines the horizontal axis of the device, (b) at least one bottom electrode located in the bottom chamber, and (c) at least one top electrode located in the top chamber, wherein each of said top electrode(s) is independently addressable and movable relative to said recording chamber in a direction that is substantially perpendicular to a plane defined by said horizontal axis of the device;
   ii) introducing into said device (a) an organotypic tissue sample characterized by a top surface and bottom surface and (b) a suitable culture medium, wherein:
      said organotypic tissue sample is disposed on said liquid permeable membrane, between said top electrode(s) and bottom electrode(s) such that said top surface faces said top electrode(s) and said bottom surface faces said bottom electrode(s), and
      said bottom electrodes(s) is/are not in direct contact with said organotypic tissue sample but is/are permanently surrounded by said culture medium;
   iii) measuring the impedance of said organotypic tissue sample at least once, wherein:
      the impedance is measured using at least one of said top electrodes and at least one of said bottom electrodes,
      the impedance is measured by transient direct electrode contact impedance recording (TDECIR), and
      said top electrode(s) is/are moved in said perpendicular direction so as to be brought into close contact with either the culture medium or the organotypic tissue sample so as to generate an appropriate impedance circuit during measurement;
   iv) optionally culturing or cultivating said organotypic tissue sample within the recording chamber before and/or after step iii); and
   v) optionally repeating step iii).

2. The method for measuring impedance in an organotypic tissue sample according to claim 1, wherein said liquid permeable membrane is fabricated from a biocompatible material.

3. The method for measuring impedance in an organotypic tissue sample according to claim 2, wherein said biocompatible material is compatible with cells and/or tissues that comprise said organotypic tissue sample without affecting cellular physiology, further wherein said biocompatible material is selected from the group consisting of polyethylene, polycarbonate, aluminium oxide, nitrocellulose, mixed cellulose esters, hydrophilic PTFE (polytetrafluorethene), polyethylennaphtalate, teflon, regenerated cellulose, cellulose acetate, nylon, silicon, polyethersulfone, most preferred the material consists of PC, Teflon, PTFE and mixtures thereof.

4. The method for measuring impedance in an organotypic tissue sample according to claim 1, wherein said liquid permeable membrane contains a plurality of pores that range in size from 0.02 and 200 um.

5. The method for measuring impedance in an organotypic tissue sample according to claim 1, wherein said device further comprises a computer-assisted stepping motor that automates the movement of said top electrode(s) in said top chamber in said perpendicular direction relative to said liquid permeable membrane.

6. The method for measuring impedance in an organotypic tissue sample according to claim 5, wherein said computer-assisted stepping motor automates movement and adjusts the position of said top electrode(s) in said top chamber based on the position of said organotypic tissue sample.

7. The method for measuring impedance in an organotypic tissue sample according to claim 1, wherein said top electrode(s) is/are movable in a linear fashion and in said perpendicular direction from (a) a first extended position in which a lower surface of said top electrode(s) is pressed against the upper surface of said organotypic tissue sample to (b) a second retracted position in which said lower surface is removed from said organotypic tissue.

8. The method for measuring impedance in an organotypic tissue sample according to claim 1, each of said at least one top electrode(s) comprises an elongate vertically extending portion that runs substantially perpendicular to the plane defined by the horizontal axis of the device and is connected at a lower end to a horizontally extending portion that runs substantially parallel to the plane defined by the horizontal axis of the device, wherein said horizontally extending portion comprises a lower stamping surface having a shape and surface area configured for and capable of making make direct contact with said organotypic tissue sample.

9. The method for measuring impedance in an organotypic tissue sample according to claim 8, wherein each of said at least one bottom electrode(s) comprises a horizontally extending upper stamping surface that runs substantially parallel to the plane defined by the horizontal axis of the device and faces said organotypic tissue, whereby said organotypic tissue sample is centered between said upper and lower stamping surfaces.

10. The method for measuring impedance in an organotypic tissue sample according to claim 9, wherein said respective lower and upper stamping surfaces are arranged in parallel.

11. The method for measuring impedance in an organotypic tissue sample according to claim 1, characterized in that the impedance measurement of step iii) is carried out by recording of frequency dependent impedance magnitudes and phase angles before and after application of test compounds at multiple frequencies (1 Hz 100 MHz).

12. The method for measuring impedance in an organotypic tissue sample according to claim 1, characterized in that the liquid permeable membrane comprises an opening for handling liquid and/or permitting the application or exchange of medium and test substances.

13. The method for measuring impedance in an organotypic tissue sample according to claim 1, characterized in that the organotypic tissue sample is a slice culture or explant culture derived from any mammal, vertebrate and invertebrate species of embryonic, neonatal, postnatal, and adult individuals.

14. The method for measuring impedance in an organotypic tissue sample according to claim 1, characterized in that (a) the organotypic tissue sample is transformed from a non-pathological to a pathological state, and (b) the impedance of the organotypic tissue sample is measured in accordance with step iii) at least once before and once after said transformation.

15. The method for measuring impedance in an organotypic tissue sample according to claim 14, characterized in that the transformation of the organotypic tissue sample from a non-pathological to a pathological state is carried out by:
  i) introducing one or more mutant genes into said organotypic tissue sample by means of bacterial or viral vectors,
  ii) introducing one or more disease-specific knock out of genes into said organotypic tissue sample, or
  iii) treating said organotypic tissue sample with chemical agents.

16. The method for measuring impedance in an organotypic tissue sample according to claim 14, characterized in that impedance measurement of the organotypic tissue is performed continuously.

17. The method for measuring impedance in an organotypic tissue sample according to claim 14, wherein the time span between a first impedance measurement of the organotypic tissue sample obtained prior to transformation and a second impedance measurement of the organotypic tissue sample obtained after transformation is at least 1 week.

18. The method for measuring impedance in an organotypic tissue sample according to claim 1, characterized in that (a) the organotypic tissue sample is treated with a test compound, and (b) the impedance of the organotypic tissue sample is measured in accordance with step iii) at least once before and once after said treatment.

19. The method for measuring impedance in an organotypic tissue sample according to claim 18, wherein impedance measurement is used to assess the toxicity of the test compound.

20. The method for measuring impedance in an organotypic tissue sample according to claim 18, wherein the time span between a first impedance measurement of the organotypic tissue sample obtained prior to treatment with the test compound and a second impedance measurement of the organotypic tissue sample obtained after treatment with the test compound is at least 1 week.

21. The method for measuring impedance in an organotypic tissue sample according to claim 18, characterized in that impedance measurement of the organotypic tissue is performed continuously.

22. The method for measuring impedance in an organotypic tissue sample according to claim 1, wherein (a) the organotypic tissue sample introduced into said device in step (ii) is in a non-pathological state, and (b) the method includes the step of:
  i) measuring the impedance of said non-pathological organotypic tissue sample as set forth in step (iii);
  ii) transforming said organotypic tissue sample to a pathological state and measuring the impedance of said transformed organotypic tissue sample via the procedure set forth in step (iii);
  iii) treating said transformed organotypic tissue sample with a test compound and then measuring the impedance of said transformed organotypic tissue sample a second time, again via the procedure set forth in step (iii).

23. The method for measuring impedance in an organotypic tissue sample according to claim 1, characterized in that the organotypic tissue sample is obtained from a transgenic animal carrying one or more mutation-inducing properties characteristic of a neurogenerative diseases selected from the group consisting of Alzheimer's disease, Parkinson's disease, Huntington's disease, amyotrophic lateral sclerosis, prion diseases, Pick's disease, fronto-temporal dementia, progressive nuclear palsy, corticobasal degeneration, multiple system atrophy, mild-cognitive impairment, ischemic stroke, multiple sclerosis, motor neuron diseases, nerve injury and repair, age related macular degenerations, rod-cone dystrophy, cone-rod dystrophy, retinitis pigmentosa, glaucoma, and other retina associated degenerations.

24. The method for measuring impedance in an organotypic tissue sample according to claim 1, wherein said top and bottom electrode(s) is/are interconnected by at least one multiplexer and an impedance/gain-phase analyzer system.

25. The method for measuring impedance in an organotypic tissue sample according to claim 1, characterized in that the at least one bottom electrode(s) is/are supported on a substrate at the bottom of the recording chamber.

26. The method for measuring impedance in an organotypic tissue sample according to claim 1, characterized in that the recording chamber is connected to an automated liquid handling system.

27. The method for measuring impedance in an organotypic tissue sample according to claim 26, characterized in that the liquid handling system can provide a humidified atmosphere in the recording chamber or the liquid handling system is placed in an $CO_2$ incubator.

28. The method for measuring impedance in an organotypic tissue sample according to claim 1, wherein the device of step i) comprises a bottomless multiwell frame with 2-1000 wells, wherein each well defines one recording chamber.

29. The method for measuring impedance in an organotypic tissue sample according to claim 28, characterized in that the liquid permeable membrane extends through all of the recording chambers.

30. The method for measuring impedance in an organotypic tissue sample according to claim 1, wherein each of said recording chamber(s) further comprise an upper lid.

31. The method for measuring impedance in an organotypic tissue sample according to claim 30, wherein each of said recording chamber upper lid(s) further comprise an opening therein.

32. The method for measuring impedance in an organotypic tissue sample according to claim 30, wherein said upper lid contains an implemented multiplexer board.

33. The method for measuring impedance in an organotypic tissue sample according to claim 1, characterized in that the at least one bottom electrode(s) is/are connected to connection pads via conductors, wherein the conductors are isolated from each other by a passivation layer comprising silicon nitride, silicon oxide, polyimide, or viscose polymers.

34. The method for measuring impedance in an organotypic tissue sample according to claim 1, characterized in that the number of bottom measurement in the recording chamber ranges from 4 to 256.

* * * * *

SEQUENCE LISTING

<160> NUMBER OF SEQ ID NOS: 3

<210> SEQ ID NO 1
<211> LENGTH: 383
<212> TYPE: PRT
<213> ORGANISM: homo sapiens

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125
```

Glu Pro Pro Lys Ser Gly Asp Arg Ser Gly Tyr Ser Ser Pro Gly Ser
            130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Ile Asn Lys Lys Leu
210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
            275                 280                 285

Lys Asp Arg Val Gln Ser Lys Ile Gly Ser Leu Asp Asn Ile Thr His
            290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
            355                 360                 365

Thr Leu Ala Asp Glu Val Ser Ala Ser Leu Ala Lys Gln Gly Leu
            370                 375                 380

<210> SEQ ID NO 2
<211> LENGTH: 441
<212> TYPE: PRT
<213> ORGANISM: homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

```
Ser Lys Ser Lys Asp Gly Thr Gly Ser Asp Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
                275                 280                 285

Ser Lys Cys Gly Ser Lys Asp Asn Ile Lys His Val Pro Gly Gly Gly
                290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
    435                 440

<210> SEQ ID NO 3
<211> LENGTH: 31
<212> TYPE: PRT
<213> ORGANISM: homo sapiens

<400> SEQUENCE: 3

Val Gln Ile Ile Asn Lys Lys Leu Asp Leu Ser Asn Val Gln Ser Lys
1               5                   10                  15

Cys Gly Ser Lys Asp Asn Ile Lys His Val Leu Gly Gly Gly Ser
                20                  25                  30
```